United States Patent
Naidu et al.

(10) Patent No.: US 9,932,353 B2
(45) Date of Patent: Apr. 3, 2018

(54) IMIDAZOPYRIMIDINE MACROCYCLES AS INHIBITORS OF HUMAN IMMUNODEFICIENCY VIRUS REPLICATION

(71) Applicant: VIIV HEALTHCARE UK (NO. 5) LIMITED, Brentford, Middlesex (GB)

(72) Inventors: B. Narasimhulu Naidu, Wallingford, CT (US); Manoj Patel, Wallingford, CT (US)

(73) Assignee: ViiV HEALTHCARE UK (NO. 5) LIMITED, Brentford, Middlesex (GB)

( * ) Notice: Subject to any disclaimer, the term of this patent is extended or adjusted under 35 U.S.C. 154(b) by 25 days.

(21) Appl. No.: 15/119,446

(22) PCT Filed: Feb. 13, 2015

(86) PCT No.: PCT/US2015/015895
§ 371 (c)(1),
(2) Date: Aug. 17, 2016

(87) PCT Pub. No.: WO2015/126758
PCT Pub. Date: Aug. 27, 2015

(65) Prior Publication Data
US 2017/0015681 A1   Jan. 19, 2017

Related U.S. Application Data

(60) Provisional application No. 61/940,912, filed on Feb. 18, 2014.

(51) Int. Cl.
*C07D 498/22* (2006.01)
*A61K 31/529* (2006.01)
*A61K 45/06* (2006.01)

(52) U.S. Cl.
CPC .......... *C07D 498/22* (2013.01); *A61K 31/529* (2013.01); *A61K 45/06* (2013.01)

(58) Field of Classification Search
CPC combination set(s) only.
See application file for complete search history.

(56) References Cited

U.S. PATENT DOCUMENTS

| 9,273,067 B2 * | 3/2016 | Naidu | C07D 498/22 |
| 9,409,922 B2 * | 8/2016 | Peese | C07D 498/22 |
| 2013/0231331 A1 | 9/2013 | Pendri et al. | |
| 2014/0051692 A1 * | 2/2014 | Naidu | A61K 31/519 |
| | | | 514/229.5 |

FOREIGN PATENT DOCUMENTS

WO   WO 2012/065963 A2   5/2012

* cited by examiner

*Primary Examiner* — Amanda L Aguirre
(74) *Attorney, Agent, or Firm* — Robert H. Brink; Edward R. Gimmi; William R. Majarian

(57) ABSTRACT

The disclosure generally relates to compounds of formula I, including compositions and methods for treating human immunodeficiency virus (HIV) infection. The disclosure provides novel inhibitors of HIV, pharmaceutical compositions containing such compounds, and methods for using these compounds in the treatment of HIV infection.

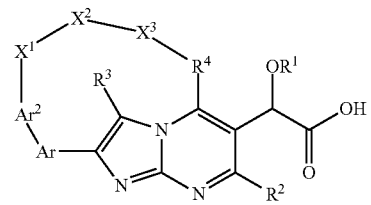

13 Claims, No Drawings

IMIDAZOPYRIMIDINE MACROCYCLES AS INHIBITORS OF HUMAN IMMUNODEFICIENCY VIRUS REPLICATION

CROSS-REFERENCE TO RELATED APPLICATIONS

This application is a 371 of International Application No. PCT/US2015/015895, filed 13 Feb. 2015, which claims the benefit of U.S. Provisional Application No. 61/940,912, filed 18 Feb. 2014, which are incorporated herein in their entireties.

BACKGROUND OF THE INVENTION

The disclosure generally relates to compounds, compositions, and methods for the treatment of human immunodeficiency virus (HIV) infection. The disclosure provides novel inhibitors of HIV, pharmaceutical compositions containing such compounds, and methods for using these compounds in the treatment of HIV infection.

Human immunodeficiency virus (HIV) has been identified as the etiological agent responsible for acquired immune deficiency syndrome (AIDS), a fatal disease characterized by destruction of the immune system and the inability to fight off life threatening opportunistic infections. Recent statistics indicate that as many as 35.3 million people worldwide are infected with the virus (UNAIDS Report on the Global AIDS Epidemic 2013). In addition to the large number of individuals already infected, the virus continues to spread. Estimates from 2012 point to close to 2.3 million new infections in that year alone. In the same year there were approximately 1.6 million deaths associated with HIV and AIDS.

There are currently a number of antiviral drugs available to combat the infection. These drugs can be divided into classes based on the viral protein they target or their mode of action. In particular, saquinavir, indinavir, ritonavir, nelfinavir atazanavir darunavir, amprenavir, fosamprenavir, lopinavir and tipranavir are competitive inhibitors of the aspartyl protease expressed by HIV. Zidovudine, didanosine, stavudine, lamivudine, zalcitabine, emtricitibine, tenofovir and abacavir are nucleos(t)ide reverse transcriptase inhibitors that behave as substrate mimics to halt viral cDNA synthesis. The non-nucleoside reverse transcriptase inhibitors nevirapine, delavirdine, efavirenz and etravirine inhibit the synthesis of viral cDNA via a non-competitive (or uncompetitive) mechanism. Enfuvirtide and maraviroc inhibit the entry of the virus into the host cell. An HIV integrase inhibitor, raltegravir (MK-0518, Isentress®), has also been approved for use in treatment experienced patients, and it is clear that this class of inhibitors is very effective as part of a combination regimen containing HIV inhibitors of different classes.

Used alone, these drugs are effective in reducing viral replication: However, the effect is only temporary as the virus readily develops resistance to all known agents used as monotherapy. On the other hand, combination therapy has proven very effective at both reducing virus and suppressing the emergence of resistance in a number of patients. In the US, where combination therapy is widely available, the number of HIV-related deaths has dramatically declined (Palella, F. J.; Delany, K. M.; Moorman, A. C.; Loveless, M. O.; Furher, J.; Satten, G. A.; Aschman, D. J.; Holmberg, S. D. *N. Engl. J. Med.* 1998, 338, 853-860).

Unfortunately, not all patients are responsive and a large number fail this therapy. In fact, initial studies suggest that approximately 30-50% of patients ultimately fail at least one drug in the suppressive combination. Treatment failure in most cases is caused by the emergence of viral resistance. Viral resistance in turn is caused by the replication rate of HIV-1 during the course of infection combined with the relatively high viral mutation rate associated with the viral polymerase and the lack of adherence of HIV-infected individuals in taking their prescribed medications. Clearly, there is a need for new antiviral agents, preferably with activity against viruses already resistant to currently approved drugs. Other important factors include improved safety and a more convenient dosing regimen than many of the currently approved drugs.

Compounds which inhibit HIV replication have been disclosed. See WO2007131350, WO2009062285, WO2009062288, WO2009062289, WO2009062308, WO2010130842, WO2011076765, WO2012003497, WO2012003498, WO2012033735, WO2012065963, WO2012066442, WO2013012649, WO2013043553, WO2013062028, WO2013073875, WO2013134113, WO2013134142, WO2014021867, WO20140028384, and WO2014164428.

The invention provides technical advantages, for example, the compounds are novel and are useful in the treatment of HIV. Additionally, the compounds provide advantages for pharmaceutical uses, for example, with regard to one or more of their mechanism of action, binding, inhibition efficacy, target selectivity, solubility, safety profiles, or bioavailability.

DESCRIPTION OF THE INVENTION

The invention encompasses compounds of Formula I, including pharmaceutically acceptable salts, their pharmaceutical compositions, and their use in inhibiting HIV integrase and treating those infected with HIV or AIDS.

One aspect of the invention is a compound of Formula I

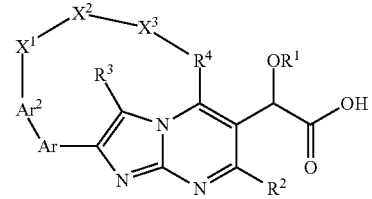

where:
$R^1$ is hydrogen, alkyl, or cycloalkyl;
$R^2$ is hydrogen or alkyl;
$R^3$ is hydrogen, alkyl or halo;
$R^4$ is cycloalkyl or $Ar^3$;
or $R^4$ is azetidinyl, pyrrolidinyl, piperidinyl, piperazinyl, morpholinyl, homopiperidinyl, homopiperazinyl, or homomorpholinyl, and is substituted with 0-3 alkyl substituents;
$R^5$ is hydrogen or alkyl;
$Ar^1$ is phenyl substituted with 0-3 substituents selected from cyano, halo, alkyl, haloalkyl, alkoxy, and haloalkoxy;
$Ar^2$ is phenyl, pyridinyl, pyridazinyl, pyrimidinyl, pyrazinyl, or trizainyl, and is substituted with 0-3 substituents selected from cyano, halo, alkyl, haloalkyl, alkoxy, haloalkoxy, and $CON(R^5)_2$;

Ar³ is phenyl, chromanyl, or dihydrobenzoxazinyl, and is substituted with 0-3 substituents selected from cyano, halo, alkyl, haloalkyl, alkoxy, and haloalkoxy;
$X^1$ is CH, $CH_2$, O, S, or $NR^5$;
$X^2$ is alkylene or alkenylene; and
$X^3$ is CH, $CH_2$, $CH_2O$, O, S, or $NR^5$;
or a pharmaceutically acceptable salt thereof.

Another aspect of the invention is a compound of Formula I where:
$R^1$ is hydrogen or alkyl;
$R^2$ is hydrogen or alkyl;
$R^3$ is hydrogen, alkyl or halo;
$R^4$ is cycloalkyl or $Ar^3$;
or $R^4$ is azetidinyl, pyrrolidinyl, piperidinyl, piperazinyl, morpholinyl, homopiperidinyl, homopiperazinyl, or homomorpholinyl, and is substituted with 0-3 alkyl substituents;
$R^5$ is hydrogen or alkyl;
$Ar^1$ is phenyl substituted with 0-3 substituents selected from cyano, halo, alkyl, haloalkyl, alkoxy, and haloalkoxy;
$Ar^2$ is phenyl, pyridinyl, pyridazinyl, pyrimidinyl, pyrazinyl, or trizainyl, and is substituted with 0-3 substituents selected from cyano, halo, alkyl, haloalkyl, alkoxy, and haloalkoxy;
$Ar^3$ is phenyl, chromanyl, or dihydrobenzoxazinyl, and is substituted with 0-3 substituents selected from cyano, halo, alkyl, haloalkyl, alkoxy, and haloalkoxy;
$X^1$ is $CH_2$, O, S, or $NR^5$;
$X^2$ is alkylene or alkenylene; and
$X^3$ is CH, $CH_2$, O, S, or $NR^5$;
or a pharmaceutically acceptable salt thereof.

Another aspect of the invention is a compound of Formula I where $R^1$ is alkyl; $R^2$ is alkyl; $R^3$ is hydrogen; $R^4$ is $Ar^3$ or is azetidinyl, pyrrolidinyl, piperidinyl, piperazinyl, morpholinyl, homopiperidinyl, homopiperazinyl, or homomorpholinyl substituted with 0-3 alkyl substituents; $Ar^1$ is phenyl substituted with 0-3 substituents selected from cyano, halo, alkyl, haloalkyl, alkoxy, and haloalkoxy; $Ar^2$ is phenyl substituted with 0-3 substituents selected from cyano, halo, alkyl, haloalkyl, alkoxy, and haloalkoxy; $Ar^3$ is dihydrobenzoxazinyl substituted with 0-3 substituents selected from cyano, halo, alkyl, haloalkyl, alkoxy, and haloalkoxy; $X^1$ is $CH_2$ or O; $X^2$ is alkylene or alkenylene; and $X^3$ is CH, $CH_2$ or O; or a pharmaceutically acceptable salt thereof.

Another aspect of the invention is a compound of Formula I where $R^1$ is alkyl; $R^2$ is alkyl; $R^3$ is hydrogen; $R^4$ is $Ar^3$ or is piperidinyl substituted with 0-1 alkyl substituents; $Ar^1$ is phenyl; $Ar^2$ is phenyl; $Ar^3$ is dihydrobenzoxazinyl substituted with 0-1 halo or alkyl substituents; $X^1$ is $CH_2$ or O; $X^2$ is alkylene or alkenylene; and $X^3$ is CH, $CH_2$ or O; or a pharmaceutically acceptable salt thereof.

Another aspect of the invention is a compound of formula I where $R^1$ is alkyl; $R^2$ is alkyl; $R^3$ is hydrogen; $R^4$ is $Ar^3$ or is piperidinyl substituted with 0-1 alkyl substituents; $Ar^1$ is phenyl; $Ar^2$ is phenyl substituted with 0-3 substituents selected from cyano, halo, alkyl, haloalkyl, alkoxy, haloalkoxy, and $CON(R^5)_2$; $Ar^3$ is dihydrobenzoxazinyl substituted with 0-1 halo or alkyl substituents; $X^1$ is $CH_2$ or O; $X^2$ is alkylene or alkenylene; and $X^3$ is CH, $CH_2$ or O; or a pharmaceutically acceptable salt thereof.

Another aspect of the invention is a compound of Formula I where $R^1$ is alkyl, $R^2$ is alkyl and $R^3$ is hydrogen.

Another aspect of the invention is a compound of Formula I where $R^4$ is $Ar^3$ or is azetidinyl, pyrrolidinyl, piperidinyl, piperazinyl, morpholinyl, homopiperidinyl, homopiperazinyl, or homomorpholinyl substituted with 0-3 alkyl substituents.

Another aspect of the invention is a compound of Formula I where $R^4$ is $Ar^3$.

Another aspect of the invention is a compound of Formula I where $R^4$ is azetidinyl, pyrrolidinyl, piperidinyl, piperazinyl, morpholinyl, homopiperidinyl, homopiperazinyl, or homomorpholinyl substituted with 0-3 alkyl substituents.

Another aspect of the invention is a compound of Formula I where $R^4$ is piperidinyl substituted with 0-3 alkyl substituents.

Another aspect of the invention is a compound of Formula I where $Ar^1$ is phenyl substituted with 0-3 substituents selected from cyano, halo, alkyl, haloalkyl, alkoxy, and haloalkoxy.

Another aspect of the invention is a compound of Formula I where $Ar^1$ is phenyl.

Another aspect of the invention is a compound of Formula I where $Ar^2$ is phenyl substituted with 0-3 substituents selected from cyano, halo, alkyl, haloalkyl, alkoxy, haloalkoxy, and $CON(R^5)_2$.

Another aspect of the invention is a compound of Formula I where $Ar^2$ is pyridinyl, pyridazinyl, pyrimidinyl, pyrazinyl, or trizainyl, and is substituted with 0-3 substituents selected from cyano, halo, alkyl, haloalkyl, alkoxy, haloalkoxy, and $CON(R^5)_2$.

Another aspect of the invention is a compound of Formula I where $Ar^3$ is phenyl, chromanyl, or dihydrobenzoxazinyl, and is substituted with 0-3 substituents selected from cyano, halo, alkyl, haloalkyl, alkoxy, and haloalkoxy.

Another aspect of the invention is a compound of Formula I where $Ar^3$ is phenyl substituted with 0-3 substituents selected from cyano, halo, alkyl, haloalkyl, alkoxy, and haloalkoxy.

Another aspect of the invention is a compound of Formula I where $X^1$ is $CH_2$ or O; $X^2$ is alkylene or alkenylene; and $X^3$ is CH, $CH_2$ or O.

For a compound of Formula I, the scope of any instance of a variable substituent, including $R^1$, $R^2$, $R^3$, $R^4$, $R^5$, $Ar^1$, $Ar^2$, $Ar^3$, $X^1$, $X^2$, and $X^3$, can be used independently with the scope of any other instance of a variable substituent. As such, the invention includes combinations of the different aspects.

Unless specified otherwise, these terms have the following meanings "Alkyl" means a straight or branched alkyl group composed of 1 to 6 carbons. "Alkenyl" means a straight or branched alkyl group composed of 2 to 6 carbons with at least one double bond. "Alkylene" means a straight or branched divalent alkyl group composed of 1 to 6 carbons. "Alkenylene" means a straight or branched divalent alkene group composed of 2 to 6 carbons with at least one double bond. "Cycloalkyl" means a monocyclic ring system composed of 3 to 7 carbons. "Hydroxyalkyl," "alkoxy" and other terms with a substituted alkyl moiety include straight and branched isomers composed of 1 to 6 carbon atoms for the alkyl moiety. "Alkyleneoxy" means a straight or branched divalent alkyloxy group composed of 1 to 6 carbons, for example, —$CH_2CH_2CH_2O$—. "Alkenyleneoxy" means a straight or branched divalent alkeneoxy group composed of 2 to 6 carbons with at least one double bond, for example, —CH=$CHCH_2O$—. "Halo" includes fluoro, chloro, bromo, and iodo. "Halo" includes all halogenated isomers from monohalo substituted to perhalo substituted in substituents defined with halo, for example, "Haloalkyl" "haloalkoxy", "halophenyl", and "halophenoxy." "Aryl" includes carbocyclic and heterocyclic aromatic substituents. Substituents which are illustrated by chemical drawing to bond at variable positions on a multiple ring system (for example a bicyclic ring system) are intended to bond to the ring where they are drawn to append. Parenthetic and multiparenthetic terms are intended to clarify bonding relationships to those skilled in the art. For example, a term such as ((R)alkyl) means an alkyl substituent further substituted with the substituent R.

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some of the compounds of the invention exist in stereoisomeric forms. The invention includes all stereoisomeric forms of the compounds including enantiomers and diastereromers. Methods of making and separating stereoisomers are known in the art. The invention includes all tautomeric forms of the compounds. The invention includes atropisomers and rotational isomers.

The invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

Biological Methods

Inhibition of HIV Replication:

A recombinant NL-RLuc proviral clone was constructed in which a section of the nef gene from NL4-3 was replaced with the *Renilla* Luciferase gene. This virus is fully infectious and can undergo multiple cycles of replication in cell culture. In addition, the luciferous reporter provides a simple and easy method for quantitating the extent of virus growth and consequently, the antiviral activity of test compounds. The plasmid pNLRLuc contains the proviral NL-Rluc DNA cloned into pUC18 at the PvuII site. The NL-RLuc virus was prepared by transfection of 293T cells with the plasmid pNLRLuc. Transfections were performed using the LipofectAMINE PLUS kit from Invitrogen (Carlsbad, Calif.) according to the manufacturer and the virus generated was titered in MT-2 cells. For susceptibility analyses, the titrated virus was used to infect MT-2 cells in the presence of compound, and after 5 days of incubation, cells were processed and quantitated for virus growth by the amount of expressed luciferase. Assay media was RPMI 1640 supplemented with 10% heat inactivated fetal bovine serum (FBS), 100 units/ml penicillin G/100 units/ml streptomycin, 10 mM HEPES buffer pH 7.55 and 2 mM L-glutamine. The results from at least 2 experiments were used to calculate the $EC_{50}$ values. Luciferase was quantitated using the Dual Luciferase kit from Promega (Madison, Wis.). Susceptibility of viruses to compounds was determined by incubation in the presence of serial dilutions of the compound. The 50% effective concentration ($EC_{50}$) was calculated by using the exponential form of the median effect equation where $(Fa)=1/[1+(ED_{50}/drug\ conc.)^m]$ (Johnson V A, Byington R T. Infectivity Assay. In *Techniques in HIV Research*. ed. Aldovini A, Walker B D. 71-76. New York: Stockton Press. 1990). Results are shown in Table 1.

TABLE 1

| Example | $EC_{50}$ μM |
|---|---|
| 1 | 0.008 |
| 2 | 0.008 |
| 3 | 0.077 |

Pharmaceutical Composition and Methods of Use

The compounds of this invention inhibit HIV replication. Accordingly, another aspect of the invention is a method for treating HIV infection in a human patient comprising administering a therapeutically effective amount of a compound of Formula I, or a pharmaceutically acceptable salt thereof, with a pharmaceutically acceptable carrier.

Another aspect of the invention is the use of a compound of formula I in the manufacture of a medicament for the treatment of AIDS or HIV infection.

Another aspect of the invention is a method for treating HIV infection in a human patient comprising the administration of a therapeutically effective amount of a compound of Formula I, or a pharmaceutically acceptable salt thereof, with a therapeutically effective amount of at least one other agent used for treatment of AIDS or HIV infection selected from the group consisting of nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors.

Another aspect of the invention is a method wherein the agent is a nucleoside HIV reverse transcriptase inhibitor.

Another aspect of the invention is a method wherein the nucleoside HIV reverse transcriptase inhibitor is selected from the group consisting of abacavir, didanosine, emtricitabine, lamivudine, stavudine, tenofovir, zalcitabine, and zidovudine, or a pharmaceutically acceptable salt thereof.

Another aspect of the invention is a method wherein the agent is a non-nucleoside HIV reverse transcriptase inhibitor.

Another aspect of the invention is a method wherein the non-nucleoside HIV reverse transcriptase inhibitor is selected from the group consisting of delavirdine, efavirenz, and nevirapine, or a pharmaceutically acceptable thereof.

Another aspect of the invention is a method wherein the agent is an HIV protease inhibitor.

Another aspect of the invention is a method wherein the HIV protease inhibitor is selected from the group consisting of amprenavir, atazanavir, indinavir, lopinavir, nelfinavir, ritonavir, saquinavir and fosamprenavir, or a pharmaceutically acceptable salt thereof.

Another aspect of the invention is a method wherein the agent is an HIV fusion inhibitor.

Another aspect of the invention is a method wherein the HIV fusion inhibitor is enfuvirtide or T-1249, or a pharmaceutically acceptable salt thereof.

Another aspect of the invention is a method wherein the agent is an HIV attachment inhibitor.

Another aspect of the invention is a method wherein the agent is a CCR5 inhibitor.

Another aspect of the invention is a method wherein the CCR5 inhibitor is selected from the group consisting of Sch-C, Sch-D, TAK-220, PRO-140, and UK-427,857, or a pharmaceutically acceptable salt thereof.

Another aspect of the invention is a method wherein the agent is a CXCR4 inhibitor.

Another aspect of the invention is a method wherein the CXCR4 inhibitor is AMD-3100, or a pharmaceutically acceptable salt thereof.

Another aspect of the invention is a method wherein the agent is an HIV budding or maturation inhibitor.

Another aspect of the invention is a method wherein the budding or maturation inhibitor is PA-457, or a pharmaceutically acceptable salt thereof.

Another aspect of the invention is a method wherein the agent is an HIV integrase inhibitor.

Another aspect of the invention is a pharmaceutical composition comprising a therapeutically effective amount of a compound of Formula I, or a pharmaceutically acceptable salt thereof, with at least one other agent used for treatment of AIDS or HIV infection selected from the group consisting of nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors, and a pharmaceutically acceptable carrier.

Another aspect of the invention is the composition wherein the agent is a nucleoside HIV reverse transcriptase inhibitor.

Another aspect of the invention is the composition wherein the nucleoside HIV transcriptase inhibitor is selected from the group consisting of abacavir, didanosine, emtricitabine, lamivudine, stavudine, tenofovir, zalcitabine, and zidovudine, or a pharmaceutically acceptable salt thereof.

Another aspect of the invention is the composition wherein the agent is a non-nucleoside HIV reverse transcriptase inhibitor.

Another aspect of the invention is the composition wherein the non-nucleoside HIV reverse transcriptase inhibitor is selected from the group consisting of delavirdine, efavirenz, and nevirapine, or a pharmaceutically acceptable salt thereof.

Another aspect of the invention is the composition wherein the agent is an HIV protease inhibitor.

Another aspect of the invention is the composition wherein the HIV protease inhibitor is selected from the group consisting of amprenavir, atazanavir, indinavir, lopinavir, nelfinavir, ritonavir, saquinavir and fosamprenavir, or a pharmaceutically acceptable salt thereof.

Another aspect of the invention is the composition wherein the agent is an HIV fusion inhibitor.

Another aspect of the invention is the composition method wherein the HIV fusion inhibitor is enfuvirtide or T-1249, or a pharmaceutically acceptable salt thereof.

Another aspect of the invention is the composition wherein the agent is an HIV attachment inhibitor.

Another aspect of the invention is the composition wherein the agent is a CCR5 inhibitor.

Another aspect of the invention is the composition wherein the CCR5 inhibitor is selected from the group consisting of Sch-C, Sch-D, TAK-220, PRO-140, and UK-427,857, or a pharmaceutically acceptable salt thereof.

Another aspect of the invention is a method wherein the agent is a CXCR4 inhibitor.

Another aspect of the invention is a method wherein the CXCR4 inhibitor is AMD-3100 or a pharmaceutically acceptable salt thereof.

Another aspect of the invention is the composition wherein the agent is an HIV budding or maturation inhibitor.

Another aspect of the invention is the composition wherein the budding or maturation inhibitor is PA-457, or a pharmaceutically acceptable salt thereof.

Another aspect of the invention is the composition wherein the agent is an HIV integrase inhibitor.

"Combination," "coadministration," "concurrent" and similar terms referring to the administration of a compound of Formula I with at least one anti-HIV agent mean that the components are part of a combination antiretroviral therapy or highly active antiretroviral therapy (HAART) as understood by practitioners in the field of AIDS and HIV infection.

"Therapeutically effective" means the amount of agent required to provide a meaningful patient benefit as understood by practitioners in the field of AIDS and HIV infection. In general, the goals of treatment are suppression of viral load, restoration and preservation of immunologic function, improved quality of life, and reduction of HIV-related morbidity and mortality.

"Patient" means a person infected with the HIV virus and suitable for therapy as understood by practitioners in the field of AIDS and HIV infection.

"Treatment," "therapy," "regimen," "HIV infection," "ARC," "AIDS" and related terms are used as understood by practitioners in the field of AIDS and HIV infection.

The compounds of this invention are generally given as pharmaceutical compositions comprised of a therapeutically effective amount of a compound of Formula I or its pharmaceutically acceptable salt and a pharmaceutically acceptable carrier and may contain conventional excipients. A therapeutically effective amount is that which is needed to provide a meaningful patient benefit. Pharmaceutically acceptable carriers are those conventionally known carriers having acceptable safety profiles. Compositions encompass all common solid and liquid forms including capsules, tablets, losenges, and powders as well as liquid suspensions, syrups, elixers, and solutions. Compositions are made using common formulation techniques, and conventional excipients (such as binding and wetting agents) and vehicles (such as water and alcohols) are generally used for compositions. See, for example, *Remington's Pharmaceutical Sciences*, 17th edition, Mack Publishing Company, Easton, Pa. (1985).

Solid compositions are normally formulated in dosage units and compositions providing from about 1 to 1000 mg of the active ingredient per dose are preferred. Some examples of dosages are 1 mg, 10 mg, 100 mg, 250 mg, 500 mg, and 1000 mg. Generally, other antiretroviral agents will be present in a unit range similar to agents of that class used clinically. Typically, this is 0.25-1000 mg/unit.

Liquid compositions are usually in dosage unit ranges. Generally, the liquid composition will be in a unit dosage range of 1-100 mg/mL. Some examples of dosages are 1 mg/mL, 10 mg/mL, 25 mg/mL, 50 mg/mL, and 100 mg/mL. Generally, other antiretroviral agents will be present in a unit range similar to agents of that class used clinically. Typically, this is 1-100 mg/mL.

The invention encompasses all conventional modes of administration; oral and parenteral methods are preferred. Generally, the dosing regimen will be similar to other antiretroviral agents used clinically. Typically, the daily dose will be 1-100 mg/kg body weight daily. Generally, more compound is required orally and less parenterally. The specific dosing regime, however, will be determined by a physician using sound medical judgement.

The invention also encompasses methods where the compound is given in combination therapy. That is, the compound can be used in conjunction with, but separately from, other agents useful in treating AIDS and HIV infection. Some of these agents include HIV attachment inhibitors, CCR5 inhibitors, CXCR4 inhibitors, HIV cell fusion inhibitors, HIV integrase inhibitors, HIV nucleoside reverse transcriptase inhibitors, HIV non-nucleoside reverse transcriptase inhibitors, HIV protease inhibitors, budding and maturation inhibitors, immunomodulators, and anti-infectives. In these combination methods, the compound of Formula I will generally be given in a daily dose of 1-100 mg/kg body weight daily in conjunction with other agents. The other agents generally will be given in the amounts used therapeutically. The specific dosing regime, however, will be determined by a physician using sound medical judgement.

Synthetic Methods

The compounds of this invention can be made by various methods known in the art including those of the following schemes and in the specific embodiments section. The structure numbering and variable numbering shown in the synthetic schemes are distinct from, and should not be confused with, the structure or variable numbering in the claims or the rest of the specification. The variables in the schemes are meant only to illustrate how to make some of the compounds of this invention. The disclosure is not limited to the foregoing illustrative examples and the examples should be considered in all respects as illustrative and not restrictive, reference being made to the appended claims, rather than to the foregoing examples, and all changes which come within the meaning and range of equivalency of the claims are therefore intended to be embraced.

Abbreviations used in the schemes and examples generally follow conventions used in the art. Chemical abbreviations used in the specification and examples are defined as follows: "KHMDS" for potassium bis(trimethylsilyl)amide; "DMF" for N,N-dimethylformamide; "HATU" for O-(t-Azabenzotriazol-1-yl)-N,N,N',N'-tetramethyluronium hexafluorophosphate, "MeOH" for methanol; "Ar" for aryl; "TFA" for trifluoroacetic acid, "DMSO" for dimethylsulfoxide; "h" for hours; "rt" for room temperature or retention time (context will dictate); "min" for minutes; "EtOAc" for ethyl acetate; "THF" for tetrahydrofuran; "Et$_2$O" for diethyl ether; "DMAP" for 4-dimethylaminopyridine; "DCM" for dichloromethane, "DCE" for 1,2-dichloroethane; "ACN" for acetonitrile; "DME" for 1,2-dimethoxyethane; "HOBt" for 1-hydroxybenzotriazole hydrate; "DIEA" for diisopropylethylamine, "DEAD" for diethyl azodicarboxylate and "DIAD" for diisopropyl azodicarboxylate.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "µL" for microliter or microliters, "N" for normal, "M" for molar, "mmol" for millimole or millimoles, "atm" for atmosphere, "psi" for pounds per square inch, "conc." for concentrate, "sat" or "sat'd" for saturated, "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

Some compounds can be synthesized from an appropriately substituted heterocycle I-1 according to Scheme I. Compound I-1 and I-2 are commercially available or synthesized by reactions known in the art. Intermediates I-3 were prepared by procedures known in the art or as set forth in the examples below using compound I-1 and compound I-2. Intermediates I-3 were transformed to intermediates I-5 via intermediates I-4 using conditions known to those skilled in the art. Intermediates I-5 were converted to intermediates I-6 by reactions known in the art, including Davis oxidation. Intermediates I-6 were oxidized to intermediates I-7 by known conditions, including Dess-Martin oxidation. Intermediates I-7 were reduced to chiral intermediates I-8 using known conditions in the presence of catalytic chiral ligands. Intermediates I-8 were converted to the intermediates I-9 by known conditions, including tertiary-butyl acetate and perchloric acid. Sequential coupling of aryl groups to Intermediates I-9 using conditions known in the art, including Suzuki coupling, provided intermediates 10 and 11. Boronate or boronic acid coupling reagents are commercially available or were prepared by reactions known in the art (for example, PCT Appln. WO20090662285). Intermediates I-11 were converted to intermediates I-12 by conditions known in the art, including ring closing metathesis. Hydrolysis of intermediates I-12 provided products I-13 which were converted to I-14 using conditions known in the art.

Scheme I.

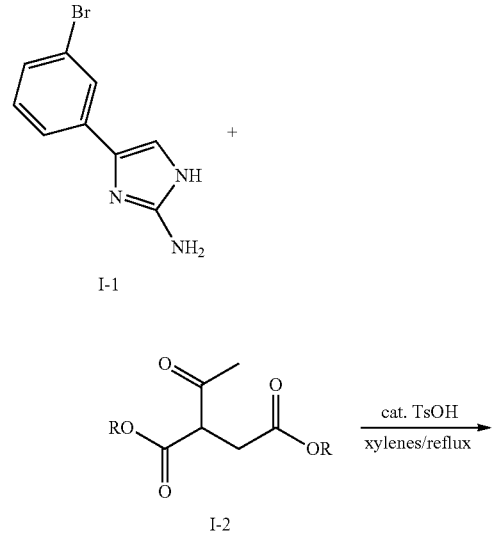

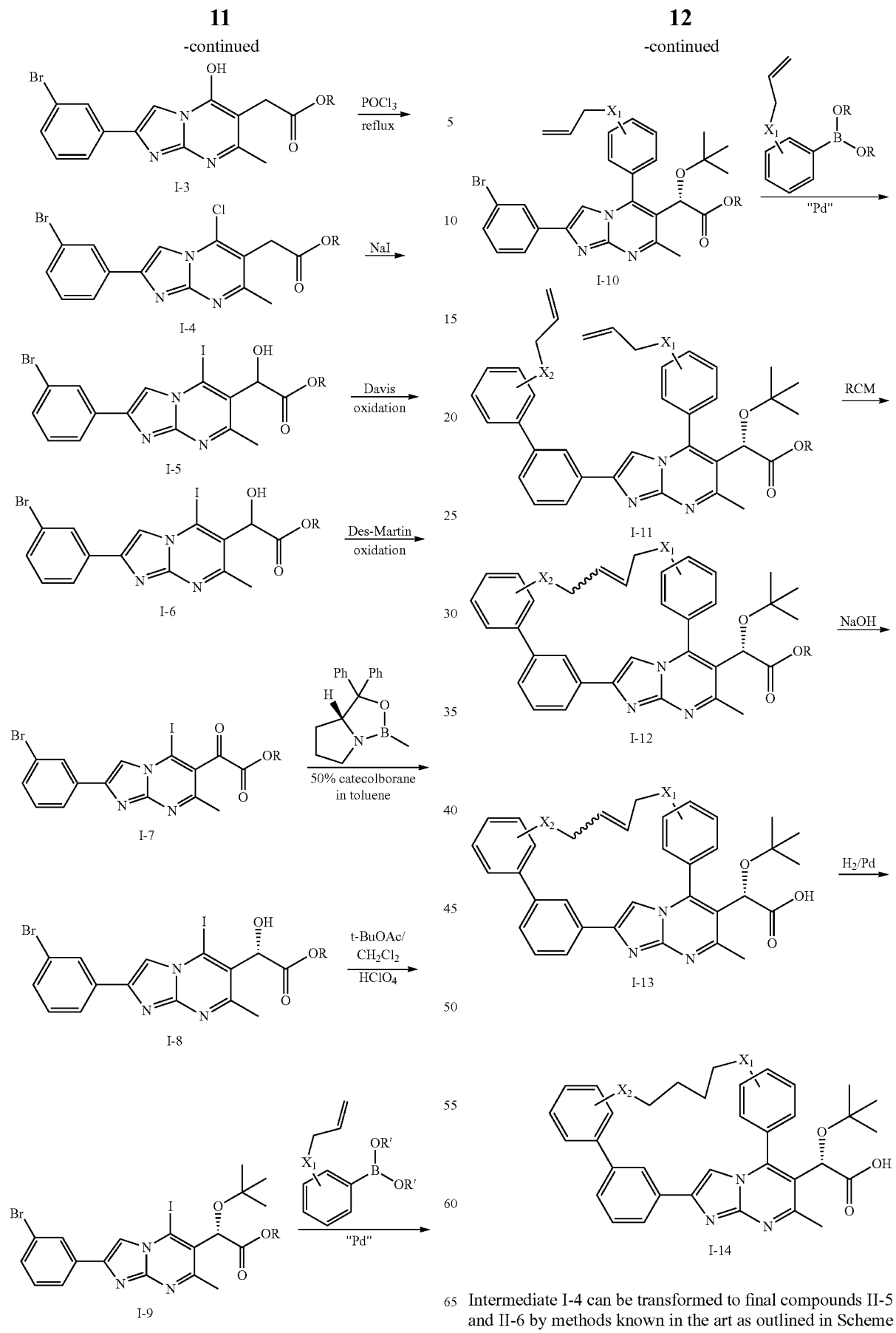
Intermediate I-4 can be transformed to final compounds II-5 and II-6 by methods known in the art as outlined in Scheme II.

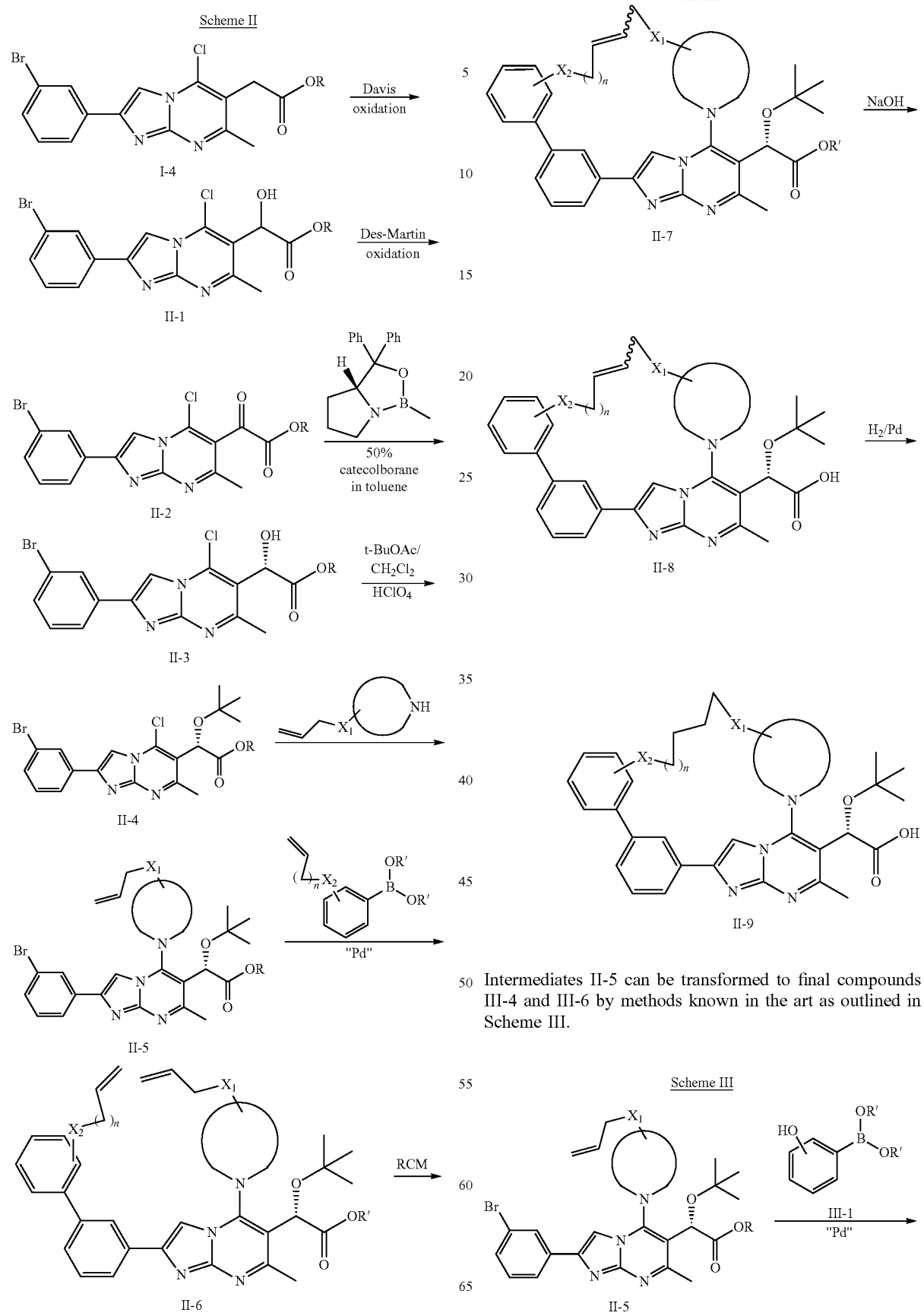
Intermediates II-5 can be transformed to final compounds III-4 and III-6 by methods known in the art as outlined in Scheme III.

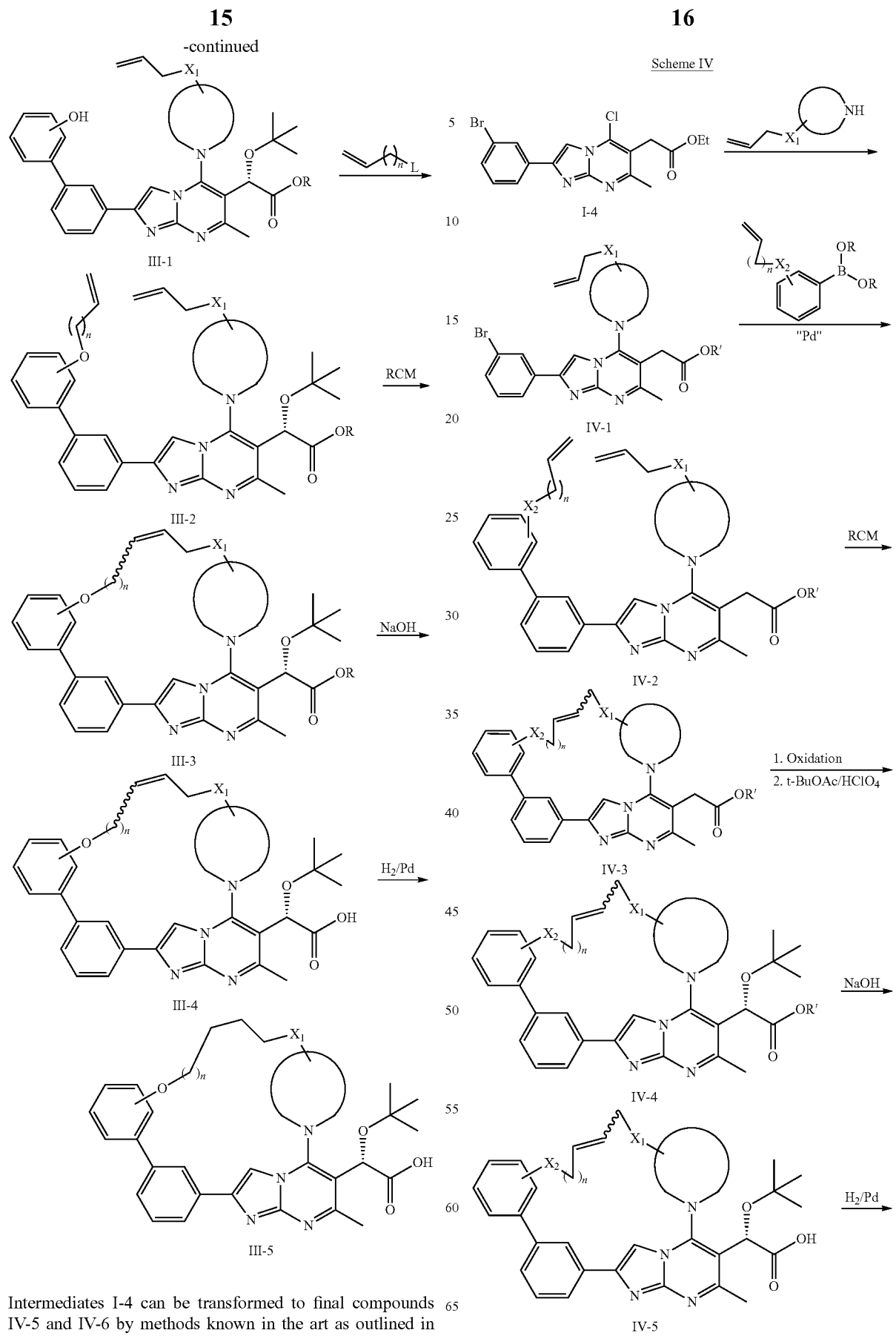
Intermediates I-4 can be transformed to final compounds IV-5 and IV-6 by methods known in the art as outlined in Scheme IV.

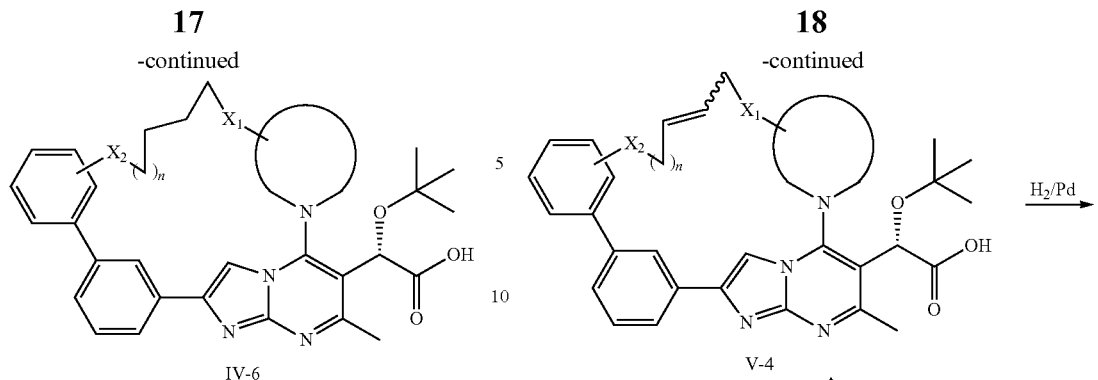

Intermediates V-1 can be transformed to final compounds V-4 and V-5 by methods known in the art as outlined in Scheme V.

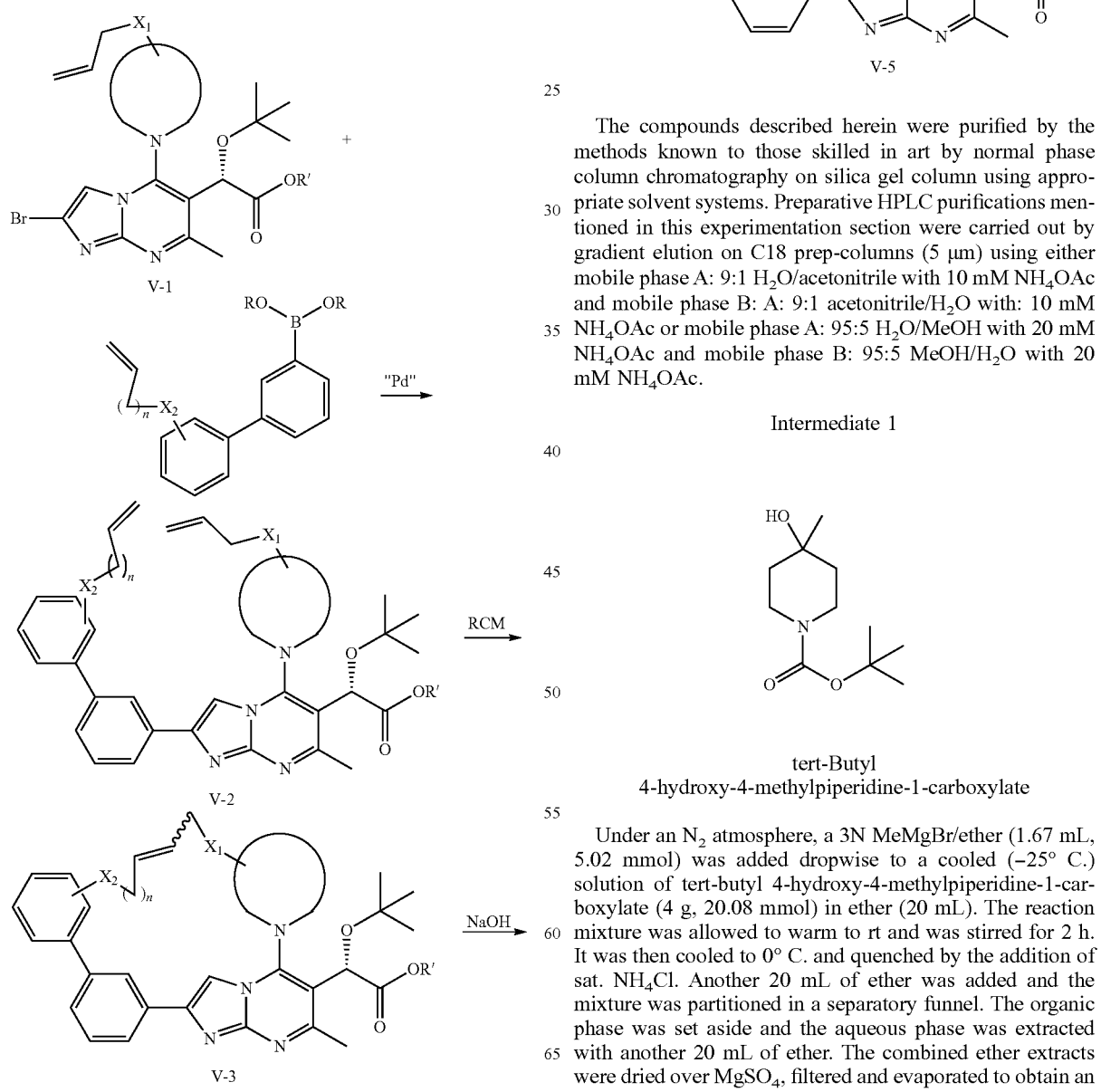

The compounds described herein were purified by the methods known to those skilled in art by normal phase column chromatography on silica gel column using appropriate solvent systems. Preparative HPLC purifications mentioned in this experimentation section were carried out by gradient elution on C18 prep-columns (5 μm) using either mobile phase A: 9:1 H$_2$O/acetonitrile with 10 mM NH$_4$OAc and mobile phase B: A: 9:1 acetonitrile/H$_2$O with: 10 mM NH$_4$OAc or mobile phase A: 95:5 H$_2$O/MeOH with 20 mM NH$_4$OAc and mobile phase B: 95:5 MeOH/H$_2$O with 20 mM NH$_4$OAc.

Intermediate 1 tert-Butyl 4-hydroxy-4-methylpiperidine-1-carboxylate

Under an N$_2$ atmosphere, a 3N MeMgBr/ether (1.67 mL, 5.02 mmol) was added dropwise to a cooled (−25° C.) solution of tert-butyl 4-hydroxy-4-methylpiperidine-1-carboxylate (4 g, 20.08 mmol) in ether (20 mL). The reaction mixture was allowed to warm to rt and was stirred for 2 h. It was then cooled to 0° C. and quenched by the addition of sat. NH$_4$Cl. Another 20 mL of ether was added and the mixture was partitioned in a separatory funnel. The organic phase was set aside and the aqueous phase was extracted with another 20 mL of ether. The combined ether extracts were dried over MgSO$_4$, filtered and evaporated to obtain an oil, which was then purified by biotage, eluting with 0-50%

EtOAc/hexane to obtain tert-butyl 4-hydroxy-4-methylpiperidine-1-carboxylate (4.30 g, 18.0 mmol, 90% yield) as a colorless oil. $^1$H NMR (500 MHz, CDCl$_3$) δ 3.84-3.65 (m, 2H), 3.34-3.18 (m, 2H), 2.59-2.39 (m, 1H), 1.61-1.53 (m, 4H), 1.50-1.45 (m, 9H), 1.32-1.27 (m, 3H).

Intermediate 2

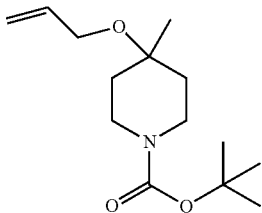 [SMILES: C=CCOC1(C)CCN(C(=O)OC(C)(C)C)CC1]

tert-Butyl 4-(allyloxy)-4-methylpiperidine-1-carboxylate

To a mixture of tert-butyl 4-hydroxy-4-methylpiperidine-1-carboxylate (4.30 g, 20.0 mmol) in DMF (50 mL) at 0° C. was added NaH (60 wt %) (1.60 g, 39.9 mmol). The mixture was then stirred at rt for 2 h. At this time allyl bromide (8.64 mL, 100 mmol) was added slowly over the course of 5 min. The reaction mixture was stirred at rt for 3 h. It was then cooled to 0° C. and quenched with sat. NH$_4$Cl. The reaction mixture was extracted with ether. The organic phase was dried over MgSO$_4$, filtered and concentrated to obtain a colorless oil, which was then purified by biotage, eluting with 0-25% EtOAc/hexane to isolate 3.1 g (61%) of tert-butyl 4-(allyloxy)-4-methylpiperidine-1-carboxylate as a colorless oil. $^1$H NMR (500 MHz, CDCl$_3$) δ 6.02-5.90 (m, 1H), 5.32 (dd, J=17.2, 1.7 Hz, 1H), 5.16 (dd, J=10.4, 1.4 Hz, 1H), 3.94-3.88 (m, 2H), 3.73 (br. s., 2H), 3.19 (br. s., 2H), 1.78 (d, J=13.1 Hz, 2H), 1.53-1.42 (m, 11H), 1.21 (s, 3H).

Intermediate 3

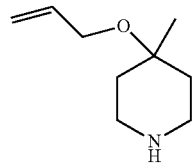

4-(Allyloxy)-4-methylpiperidine Hydrochloride

A mixture of tert-butyl 4-(allyloxy)-4-methylpiperidine-1-carboxylate (3.10 g, 12.1 mmol) and 4N HCl/dioxane (15 mL, 60.0 mmol) was stirred at rt for 3 h. It was then concentrated in vacuum to obtain 2.2 g (95%) of 4-(allyloxy)-4-methylpiperidine hydrochloride as a light brown solid. $^1$H NMR (500 MHz, METHANOL-d$_4$) δ 6.02-5.92 (m, 1H), 5.33 (dd, J=17.2, 1.7 Hz, 1H), 5.15 (dd, J=10.6, 1.7 Hz, 1H), 3.96 (dt, J=5.1, 1.6 Hz, 2H), 3.23-3.18 (m, 4H), 2.06 (dd, J=15.3, 2.5 Hz, 2H), 1.77-1.69 (m, 2H), 1.31-1.28 (s, 3H).

Intermediate 4

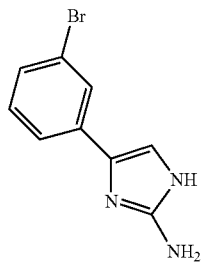 [SMILES: Nc1nc(-c2cccc(Br)c2)c[nH]1]

4-(3-Bromophenyl)-1H-imidazol-2-amine

To a stirred mixture of 1H-pyrazole-1-carboximidamide, HCl (13.08 g, 89 mmol) and Na2CO3 (12.61 g, 119 mmol) in EtOH (200 mL), 200 proof) was added 2-amino-1-(3-bromophenyl)ethanone, HCl (14.9 g, 59.5 mmol) in small portions over 3 min. The resulting orange reaction mixture was stirred for 16 h at rt. Then, the resulting yellow reaction mixture concentrated and the residue was taken up in EtOAc (500 mL), washed with water (2×200 mL), brine (50 mL). The combined aq layers extracted with 10% MeOH/CH2Cl2 (4×100 mL) and combined with EtOAc layer, dried (MgSO4), filtered and concentrated to give slurry which was filtered, washed with EtOAc (50 mL) and ether (25 mL) to give yellow powder. Both LCMS and $^1$HNMR are consistent with the dimer 2,5-bis(3-bromophenyl)pyrazine (3.2 g, 8.20 mmol, 13.79% yield) as yellow solid. $^1$H NMR (500 MHz, CDCl$_3$) δ 9.08 (s, 2H), 8.29 (t, J=1.8 Hz, 2H), 7.99-8.03 (m, 2H), 7.63-7.67 (m, 2H), 7.44 (t, J=7.9 Hz, 2H). LCMS (M+H)=390.9. The filtrated was concentrated to give brown residue which was purified by flash chromatography using 5, 10 and 15% MeOH/CH$_2$Cl$_2$ to afford 4-(3-bromophenyl)-1H-imidazol-2-amine (6.35 g, 22.40 mmol, 37.7% yield) as light green foam. LCMS (M+H)=238.0

Intermediate 5

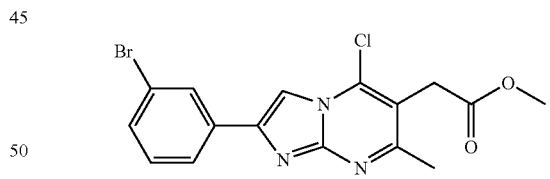

Methyl 2-(2-(3-bromophenyl)-5-chloro-7-methyl-imidazo[1,2-a]pyrimidin-6-yl)acetate A mixture of 4-(3-bromophenyl)-1H-imidazol-2-amine (6.3 g, 26.5 mmol), dimethyl 2-acetylsuccinate (7.47 g, 39.7 mmol) and Ts-OH (0.25 g, 1.314 mmol) in o-xylene (100 mL) was refluxed for 3 h. Then, cooled and treated with POCl3 (24.66 ml, 265 mmol) and N,N-dimethylaniline (6.71 ml, 52.9 mmol). The resulting mixture was heated at 120° C. for 3 h. Then, cooled, concentrated and the dark residue was dissolved in EtOAc (200 mL) and poured into ice-water (100 mL). Stirred for 5 min and carefully neutralized with Na$_2$CO$_3$, aq layer separated and organic layer washed with water (2×50 mL), brine (25 mL), dried (MgSO₄), filtered and concentrated to give dark paste which was purified by flash chromatography using 1-lit each 10, 30, 50 and 70% EtOAc/hex to give methyl 2-(2-(3-bromophenyl)-5-chloro-7-methylimidazo[1,2-a]pyrimidin-6-yl)acetate (2.119 g, 5.37 mmol, 20.29% yield) as brown foam. LCMS (M+H)=396.0.

Intermediate 6

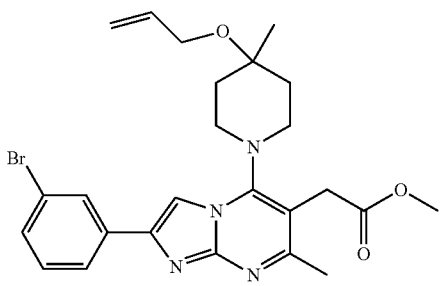 [SMILES: C=CCOC1(C)CCN(c2c(CC(=O)OC)c(C)nc3nc(-c4cccc(Br)c4)cn23)CC1]

Methyl 2-(5-(4-(allyloxy)-4-methylpiperidin-1-yl)-2-(3-bromophenyl)-7-methylimidazo[1,2-a]pyrimidin-6-yl)acetate A solution of methyl 2-(2-(3-bromophenyl)-5-chloro-7-methylimidazo[1,2-a]pyrimidin-6-yl)acetate (2.11 g, 2.94 mmol), 4-(allyloxy)-4-methylpiperidine (0.913 g, 5.88 mmol) and DIEA (1.027 ml, 5.88 mmol) in DMF (10 mL) was heated at 80° C. for 6 h. Then, cooled, diluted with ether (100 mL), washed with water (3×10 mL), brine (10 mL), dried (MgSO4), filtered, concentrated and the dark residue was purified by flash chromatography using 50, 60 and 75% EtOAc/Hex to afford two compounds with same molecular weight. Compound 2 was found to be the desired methyl 2-(5-(4-(allyloxy)-4-methylpiperidin-1-yl)-2-(3-bromophenyl)-7-methylimidazo[1,2-a]pyrimidin-6-yl)acetate, light brown solid (1.2 g, 50% purity). Re-purified by prep-HPLC to afford methyl 2-(5-(4-(allyloxy)-4-methylpiperidin-1-yl)-2-(3-bromophenyl)-7-methylimidazo[1,2-a]pyrimidin-6-yl)acetate (0.8452 g, 1.646 mmol, 56.0% yield) as white solid. ¹H NMR (500 MHz, CDCl₃) δ 8.17 (br. s., 1H), 8.02 (d, J=7.7 Hz, 1H), 7.86 (br. s., 0.5H), 7.61 (br. s., 0.5H), 7.46-7.49 (m, 1H), 7.33 (t, J=7.9 Hz, 1H), 5.97-6.19 (m, 1H), 5.51 (d, J=17.0 Hz, 0.5H), 5.35-5.43 (m, 1H), 5.23 (d, J=9.9 Hz, 0.5H), 4.02 (d, J=14.0 Hz, 2H), 3.73-3.86 (m, 6H), 3.49 (t, J=11.3 Hz, 1H), 3.21 (d, J=10.7 Hz, 1H), 2.89 (d, J=10.7 Hz, 1H), 2.60 (br. s., 1.5H), 2.56 (br. s., 1.5H), 2.03 (t, J=11.9 Hz, 2H), 1.70-1.84 (m, 2H), 1.38 (br. s., 1.5H), 1.35 (br. s., 1.5H). LCMS (M+H)=515.1.

Intermediate 7

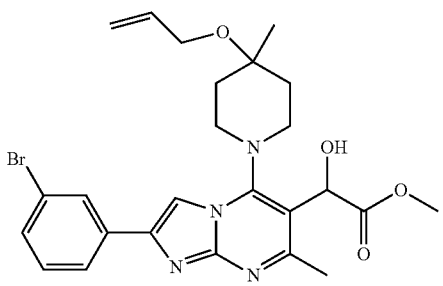 [SMILES: C=CCOC1(C)CCN(c2c(C(O)C(=O)OC)c(C)nc3nc(-c4cccc(Br)c4)cn23)CC1]

Methyl 2-(5-(4-(allyloxy)-4-methylpiperidin-1-yl)-2-(3-bromophenyl)-7-methylimidazo[1,2-a]pyrimidin-6-yl)-2-hydroxyacetate To a stirred solution of 1M KHMDS/THF (3.04 mL, 3.04 mmol) in THF (20 mL) at −78° C. was added dropwise a THF (20 mL) solution of methyl 2-(5-(4-(allyloxy)-4-methylpiperidin-1-yl)-2-(3-bromophenyl)-7-methylimidazo[1,2-a]pyrimidin-6-yl)acetate (1.2 g, 2.337 mmol) over 10 min. After 30 min, a THF (10 mL) solution of 3-phenyl-2-(phenylsulfonyl)-1,2-oxaziridine (0.794 g, 3.04 mmol) was added to the resulting dark reaction mixture and stirred for additional 30 min at −78° C. Then, the resulting dark reaction mixture was quenched with sat. NH₄Cl (20 mL), diluted with EtOAc (100 mL), washed with water (20 mL), brine (20 mL), dried (Na₂SO₄), filtered and concentrated. The residue was then purified by Biotage (5-100% EtOAc/hexane) to afford methyl 2-(5-(4-(allyloxy)-4-methylpiperidin-1-yl)-2-(3-bromophenyl)-7-methylimidazo[1,2-a]pyrimidin-6-yl)-2-hydroxyacetate (685 mg, 1.294 mmol, 55.4% yield) as off-white solid. ¹H NMR (500 MHz, CDCl₃) δ 8.15 (s, 1H), 8.04-7.99 (m, 1H), 7.52-7.46 (m, 1H), 7.33 (t, J=7.8 Hz, 1H), 6.16 (br. s., 1H), 5.58 (br. s., 1H), 5.54 (d, J=17.5 Hz, 1H), 5.43 (d, J=8.0 Hz, 1H), 4.30 (br. s., 1H), 4.03 (d, J=5.0 Hz, 2H), 3.92-3.86 (m, 1H), 3.83 (s, 3H), 3.78-3.42 (m, 2H), 2.99 (br. s., 1H), 2.71 (br. s., 3H), 2.01 (br. s., 2H), 1.80 (td, J=12.8, 4.5 Hz, 2H), 1.36 (br. s., 3H). LCMS (M+2H)=531.1.

Intermediate 8

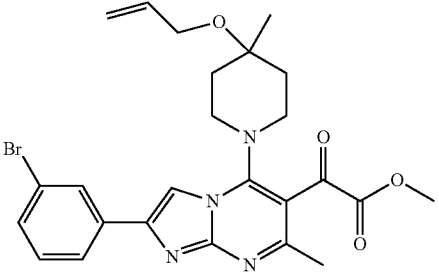 [SMILES: C=CCOC1(C)CCN(c2c(C(=O)C(=O)OC)c(C)nc3nc(-c4cccc(Br)c4)cn23)CC1]

Methyl 2-(5-(4-(allyloxy)-4-methylpiperidin-1-yl)-2-(3-bromophenyl)-7-methylimidazo[1,2-a]pyrimidin-6-yl)-2-oxoacetate To a solution of methyl 2-(5-(4-(allyloxy)-4-methylpiperidin-1-yl)-2-(3-bromophenyl)-7-methylimidazo[1,2-a]pyrimidin-6-yl)-2-hydroxyacetate (680 mg, 1.284 mmol) in CH₂Cl₂ (15 mL) was added Dess-MartinPeriodinane (654 mg, 1.541 mmol) and the resulting mixture was stirred at room temp for 3 h. Sat. NaHCO₃ solution was then added and the mixture was extracted with dichloromethane (50 mL), dried (Na₂SO₄), filtered and concentrated. The residue was then purified by Biotage (5-75% EtOAc/hexane) to afford methyl 2-(5-(4-(allyloxy)-4-methylpiperidin-1-yl)-2-(3-bromophenyl)-7-methylimidazo[1,2-a]pyrimidin-6-yl)-2-oxoacetate (608 mg, 1.153 mmol, 90% yield) as off-white solid. ¹H NMR (500 MHz, CDCl₃) δ 8.17 (t, J=1.7 Hz, 1H), 8.01 (dt, J=7.7, 1.2 Hz, 1H), 7.68 (s, 1H), 7.55-7.50 (m, 1H), 7.35 (t, J=7.9 Hz, 1H), 6.07-5.97 (m, 1H), 5.42 (dd, J=17.2, 1.7 Hz, 1H), 5.27 (dd, J=10.4, 1.6 Hz, 1H), 4.00 (s, 2H), 3.98 (s, 3H), 3.53 (t, J=11.6 Hz, 2H), 3.23 (d, J=11.8 Hz, 2H), 2.60 (s, 3H), 2.03 (d, J=12.8 Hz, 2H), 1.79-1.68 (m, 2H), 1.35 (s, 3H). LCMS (M+2H)=529.1.

Intermediate 9

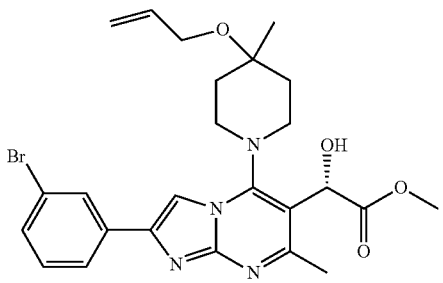 [SMILES: C=CCOC1(C)CCN(c2c([C@H](O)C(=O)OC)c(C)nc3nc(-c4cccc(Br)c4)cn23)CC1]

(S)-Methyl 2-(5-(4-(allyloxy)-4-methylpiperidin-1-yl)-2-(3-bromophenyl)-7-methylimidazo[1,2-a]pyrimidin-6-yl)-2-hydroxyacetate To a stirred yellow solution of methyl 2-(5-(4-(allyloxy)-4-methylpiperidin-1-yl)-2-(3-bromophenyl)-7-methylimidazo[1,2-a]pyrimidin-6-yl)-2-oxoacetate (600 mg, 1.138 mmol) in anhydrous toluene (15 mL) was added 1M (R)-1-methyl-3,3-diphenylhexahydropyrrolo[1,2-a][1,3,2]oxazaborole/toluene (0.455 mL, 0.455 mmol). The mixture was cooled to −35° C. and a solution of catechoborane 50% in toluene (0.390 mL, 1.593 mmol) was added over 5 min. After 30 min, the reaction mixture was slowly warmed to −15° C. and stirred for additional 2 h. At this point LCMS indicated approx 40% conversion. Mixture was then let it sit in a refrigerator (−15 to −20° C.) for 16 h. At his point LCMS indicated completion of reaction. The mixture was then diluted with EtOAc (100 mL) and sat. Na$_2$CO$_3$ (30 mL). The mixture was stirred vigorously for 30 min, and the organic phase washed with sat Na$_2$CO$_3$ (2×20 mL), dried (Na$_2$SO$_4$), filtered, concentrated and the residue was purified by silica gel chromatography (5-70% EtOAc/hexane) to afford desired (S)-methyl 2-(5-(4-(allyloxy)-4-methylpiperidin-1-yl)-2-(3-bromophenyl)-7-methylimidazo[1,2-a]pyrimidin-6-yl)-2-hydroxyacetate as off-white solid. $^1$H NMR (500 MHz, CDCl$_3$) δ 8.15 (s, 1H), 8.04-7.99 (m, 1H), 7.52-7.46 (m, 1H), 7.33 (t, J=7.8 Hz, 1H), 6.16 (br. s., 1H), 5.58 (br. s., 1H), 5.54 (d, J=17.5 Hz, 1H), 5.43 (d, J=8.0 Hz, 1H), 4.30 (br. s., 1H), 4.03 (d, J=5.0 Hz, 2H), 3.92-3.86 (m, 1H), 3.83 (s, 3H), 3.78-3.42 (m, 2H), 2.99 (br. s., 1H), 2.71 (br. s., 3H), 2.01 (br. s., 2H), 1.80 (td, J=12.8, 4.5 Hz, 2H), 1.36 (br. s., 3H). LCMS (M+2H)=531.1.

Intermediate 10

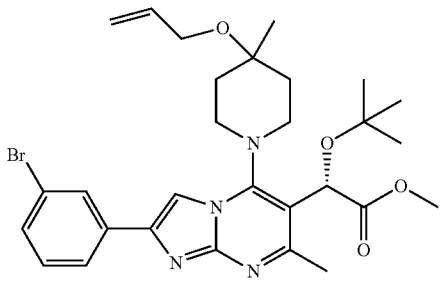 [SMILES: C=CCOC1(C)CCN(c2c([C@H](OC(C)(C)C)C(=O)OC)c(C)nc3nc(-c4cccc(Br)c4)cn23)CC1]

(S)-Methyl 2-(5-(4-(allyloxy)-4-methylpiperidin-1-yl)-2-(3-bromophenyl)-7-methylimidazo[1,2-a]pyrimidin-6-yl)-2-(tert-butoxy)acetate A mixture of (S)-methyl 2-(5-(4-(allyloxy)-4-methylpiperidin-1-yl)-2-(3-bromophenyl)-7-methylimidazo[1,2-a]pyrimidin-6-yl)-2-hydroxyacetate (490 mg, 0.926 mmol) and 70% HClO$_4$ (0.087 mL, 1.018 mmol) in anhydrous CH$_2$Cl$_2$ (30 mL) was cooled in ice-water bath and saturated with isobutylene by bubbling through the reaction mixture for 10 min. After 2 h cold bath was removed and the yellow reaction mixture was stirred at rt for 14 h. Mixture was then neutralized with sat Na$_2$CO$_3$ (50 mL), org layer separated, dried (Na$_2$SO$_4$), filtered, concentrated and purified by flash chromatography (5-100% EtOAc/hexane) to afford (S)-methyl 2-(5-(4-(allyloxy)-4-methylpiperidin-1-yl)-2-(3-bromophenyl)-7-methylimidazo[1,2-a]pyrimidin-6-yl)-2-(tert-butoxy)acetate (180 mg, 0.307 mmol, 33.2% yield) as off-white solid. $^1$H NMR (500 MHz, CDCl$_3$) δ 8.15 (s, 1H), 8.01 (d, J=7.9 Hz, 1H), 7.92 (s, 0.8H), 7.60 (s, 0.2H), 7.51-7.43 (m, 1H), 7.33 (t, J=7.9 Hz, 1H), 6.21-6.07 (m, 0.8H), 6.10-5.97 (m, 0.2H), 5.93 (s, 1H), 5.59 (s, 0.2H), 5.54 (d, J=16.9 Hz, 0.8H), 5.42 (d, J=9.9 Hz, 0.8H), 5.38 (s, 0.2H), 5.22 (d, J=9.9 Hz, 0.2H), 4.04 (d, J=4.7 Hz, 2H), 3.92 (t, J=10.6 Hz, 0.8H), 3.82-3.70 (m, 4H), 3.61-3.59 (m, 0.2H), 3.45 (br. s., 0.2H), 3.26 (br. s., 0.2H), 3.09 (d, J=9.6 Hz, 0.8H), 2.84-2.73 (m, 0.8H), 2.71 (s, 2.3H), 2.65 (s, 0.7H), 2.06-1.98 (m, 2H), 1.88-1.81 (m, 1H), 1.79-1.70 (m, 1H), 1.42 (br. s., 0.7H), 1.37 (s, 2.3H), 1.28 (s, 7H), 1.25 (br. s., 2H). LCMS (M+2H)=587.4. 80 mg of starting material was also recovered.

Intermediate 11

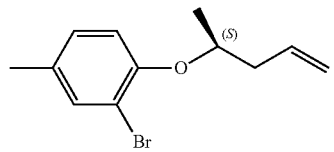

(S)-2-Bromo-4-methyl-1-(pent-4-en-2-yloxy)benzene

To a solution of 2-bromo-4-methylphenol (9.68 mL, 80 mmol) and (R)-pent-4-en-2-ol (7.60 g, 88 mmol) in THF (400 mL) was added Ph$_3$P (31.6 g, 120 mmol) followed by DEAD (19.05 mL, 120 mmol) and the resulting mixture was stirred at room temp for 16 h. Water (100 mL) was then added and the mixture was extracted with EtOAc (300 mL), washed with 1N NaOH (50 mL), brine (100 mL), dried (Na$_2$SO$_4$), filtered and concentrated. The residue was then purified via Biotage (0-10% EtOAc/hexane) to afford (S)-2-bromo-4-methyl-1-(pent-4-en-2-yloxy)benzene as light yellow oil. $^1$H NMR (500 MHz, CDCl$_3$) δ 7.40-7.37 (m, 1H), 7.05 (ddd, J=8.3, 2.1, 0.6 Hz, 1H), 6.86-6.81 (m, 1H), 5.93 (ddt, J=17.2, 10.1, 7.1 Hz, 1H), 5.19-5.08 (m, 2H), 4.40 (sxt, J=6.1 Hz, 1H), 2.60-2.51 (m, 1H), 2.46-2.38 (m, 1H), 2.29 (s, 3H), 1.36 (d, J=6.1 Hz, 3H).

Intermediate 12

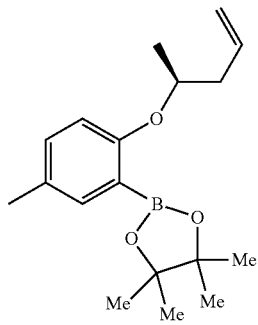 [SMILES: C=CC[C@H](C)Oc1ccc(C)cc1B1OC(C)(C)C(C)(C)O1]

(S)-4,4,5,5-Tetramethyl-2-(5-methyl-2-(pent-4-en-2-yloxy)phenyl)-1,3,2-dioxaborolane To a solution of (S)-2-bromo-4-methyl-1-(pent-4-en-2-yloxy)benzene (8.75 g, 34.3 mmol) in THF (200 mL) at −78° C. was added nBuLi, 1.6M in THF (25.7 mL, 41.2 mmol) and the mixture was stirred for 30 min. Then, 2-isopropoxy-4,4,5,5-tetramethyl-1,3,2-dioxaborolane (8.40 mL, 41.2 mmol) was added. After 30 min, cold bath was removed and reaction allowed to warm to rt. After 3 h, water (50 mL) was added and the mixture was extracted with EtOAc (300 mL). EtOAc layer was dried ($Na_2SO_4$), filtered and concentrated to afford (S)-4,4,5,5-tetramethyl-2-(5-methyl-2-(pent-4-en-2-yloxy)phenyl)-1,3,2-dioxaborolane (10 g, 33.1 mmol, 96% yield) as yellow oil. Crude was used as is in the next step without further purification. Note: Product may be volatile and not to leave under high vaccu for longer period. $^1$H NMR (500 MHz, $CDCl_3$) δ 7.46 (d, J=2.0 Hz, 1H), 7.17 (dd, J=8.4, 2.4 Hz, 1H), 6.82 (d, J=8.4 Hz, 1H), 6.03-5.93 (m, 1H), 5.14-5.04 (m, 2H), 4.35-4.29 (m, 1H), 2.56-2.48 (m, 1H), 2.40 (dt, J=13.9, 6.8 Hz, 1H), 2.30 (s, 3H), 1.37 (s, 12H), 1.30 (d, J=6.1 Hz, 3H). LCMS (M+H)=303.3.

Intermediate 13

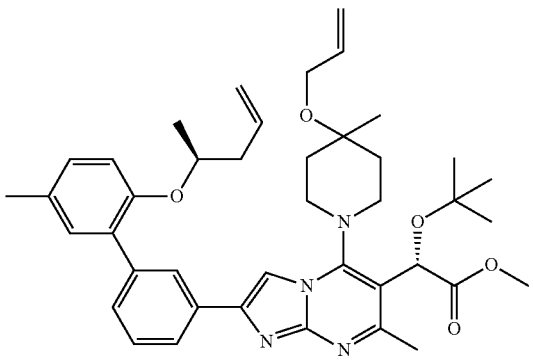

(S)-Methyl 2-(5-(4-(allyloxy)-4-methylpiperidin-1-yl)-7-methyl-2-(5'-methyl-2'-((S)-pent-4-en-2-yloxy)-[1,1'-biphenyl]-3-yl)imidazo[1,2-a]pyrimidin-6-yl)-2-(tert-butoxy)acetate A solution of ((S)-methyl 2-(5-(4-(allyloxy)-4-methylpiperidin-1-yl)-2-(3-bromophenyl)-7-methylimidazo[1,2-a]pyrimidin-6-yl)-2-(tert-butoxy)acetate (80 mg, 0.137 mmol), (S)-4,4,5,5-tetramethyl-2-(5-methyl-2-(pent-4-en-2-yloxy)phenyl)-1,3,2-dioxaborolane (61.9 mg, 0.205 mmol) and 2.0 M aq. $Na_2CO_3$ (0.171 mL, 0.342 mmol) in DMF (2 mL) was degassed for 10 min. $Pd(Ph_3P)_4$ (11.05 mg, 9.56 μmol), was added and the degassing was continued for another 5 min. The reaction was then heated at 90° C. for 3 h. At this point LCMS indicated completion of reaction. The mixture was then cooled to room temp and diluted with water (10 mL) and extracted with EtOAc (2×25 mL). The combined extracts were dried ($Na_2SO_4$), filtered, and concentrated under reduced pressure, and the residue was purified by biotage (0-60% EtOAc/hexane) to afford (S)-methyl 2-(5-(4-(allyloxy)-4-methylpiperidin-1-yl)-7-methyl-2-(5'-methyl-2'-((S)-pent-4-en-2-yloxy)-[1,1'-biphenyl]-3-yl)imidazo[1,2-a]pyrimidin-6-yl)-2-(tert-butoxy)acetate (70 mg, 0.103 mmol, 75% yield) as white foam. $^1$H NMR (500 MHz, $CDCl_3$) δ 8.15 (s, 1H), 8.02 (d, J=7.7 Hz, 1H), 7.93 (s, 1H), 7.65-7.55 (m, 1.5H), 7.51-7.43 (m, 1.5H), 7.12 (d, J=6.8 Hz, 1H), 6.93 (d, J=7.9 Hz, 1H), 6.24-6.22 (m, 0.2H), 6.12-5.99 (m, 0.8H), 5.93 (s, 0.8H), 5.88 (s, 0.2H), 5.80-5.72 (m, 1H), 5.47-5.36 (m, 1H), 5.22 (d, J=10.6 Hz, 0.2H), 5.11 (d, J=10.6 Hz, 0.8H), 5.06-4.98 (m, 2H), 4.33-4.20 (m, 1H), 4.01 (d, J=5.0 Hz, 2H), 3.93 (t, J=11.0 Hz, 1H), 3.78-3.75 (m, 2H), 3.72 (s, 3H), 3.11 (br. s., 1H), 2.81 (br. s., 1H), 2.71 (s, 2.5H), 2.66 (br. s., 0.5H), 2.44-2.39 (m, 1H), 2.38 (s, 3H), 2.26 (dd, J=13.8, 6.7 Hz, 1H), 2.05-1.97 (m, 2H), 1.88-1.69 (m, 1H), 1.28 (s, 3H), 27 (s, 7H), 1.25 (s, 2H), 1.20 (d, J=6.0 Hz, 3H). LCMS (M+H)=681.5.

Example 1

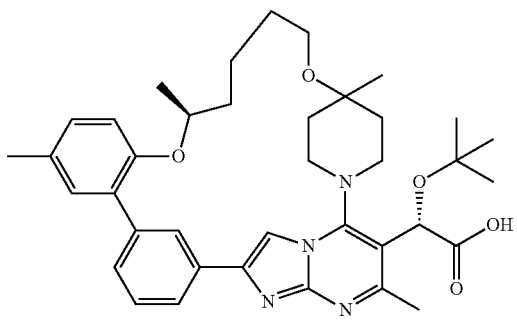 [SMILES: Cc1ccc2c(c1)-c1cccc(c1)-c1cn3c(c([C@H](OC(C)(C)C)C(=O)O)c(C)nc3n1)N1CCC(C)(CC1)OCCCC[C@H](C)O2]

(2S)-2-(tert-Butoxy)-2-[(22S)-4,17,22,28-tetramethyl-21,27-dioxa-1,5,7,34-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic Acid To a stirred solution of (S)-methyl 2-(5-(4-(allyloxy)-4-methylpiperidin-1-yl)-7-methyl-2-(5'-methyl-2'-((S)-pent-4-en-2-yloxy)-[1,1'-biphenyl]-3-yl)imidazo[1,2-a]pyrimidin-6-yl)-2-(tert-butoxy)acetate (60 mg, 0.088 mmol) and Ts-OH.$H_2O$ (33.5 mg, 0.176 mmol) in 1,2-dichloroethane (50 mL) was added Hoveyda-Grubbs catalyst 2nd generation (5.52 mg, 8.81 μmol) and heated to 70° C. for 2 h. The reaction mixture was then cooled and concentrated to about 10 mL. To this solution was added EtOH (1 mL) and $NaBH_4$ (10.00 mg, 0.264 mmol) at rt. Note: gas evoluved as soon as $NaBH_4$ was added. After 30 min added additional $NaBH_4$ (10.00 mg, 0.264 mmol) and the mixture was stirred for 3 h. LCMS at this point showed completion of reaction. The reaction mixture was diluted with EtOAc (50 mL), washed with water (3×10 mL), brine (5 mL), dried (MgSO$_4$), filtered and concentrated to give crude saturated ester as brown residue which was used in the next step without purification. LCMS (M+H)=655.5.

A mixture of above crude ester and 1N NaOH (0.441 mL, 0.441 mmol) in MeOH (2 mL) was refluxed for 4 h. Then, cooled and purified by prep-HPLC to afford desired (2S)-2-(tert-butoxy)-2-[(22S)-4,17,22,28-tetramethyl-21,27-dioxa-1,5,7,34-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid (22.8 mg, 0.036 mmol, 40.4% yield) as off-white solid. $^1$H NMR (500 MHz, DMSO-d$_6$) δ 8.21 (s, 1H), 8.06 (d, J=7.7 Hz, 1H), 7.98 (s, 1H), 7.54 (t, J=7.9 Hz, 1H), 7.36 (d, J=7.7 Hz, 1H), 7.19 (s, 1H), 7.14 (d, J=8.8 Hz, 1H), 7.05 (d, J=8.4 Hz, 1H), 5.79 (s, 1H), 4.62 (br. s., 1H), 3.80 (t, J=11.2 Hz, 1H), 3.67-3.57 (m, 1H), 3.51-3.42 (m, 3H), 3.26-3.12 (m, 1H), 2.58 (s, 3H), 2.29 (s, 3H), 1.95 (d, J=12.1 Hz, 1H), 1.89-1.55 (m, 9H), 1.22 (s, 3H), 1.19 (s, 9H), 1.08 (d, J=6.2 Hz, 3H). LCMS (M+H)=641.5.

Intermediate 14

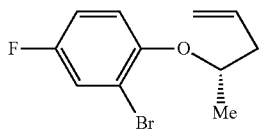

(S)-2-Bromo-4-fluoro-1-(pent-4-en-2-yloxy)benzene

To a solution of 2-bromo-4-fluorophenol (5.61 g, 29.4 mmol), (R)-pent-4-en-2-ol (2.3 mL, 26.7 mmol), and PPh$_3$ (9.81 g, 37.4 mmol) in THF (90 mL) was added DEAD (14.8 mL, 37.4 mmol). After stirring 17 h, the yellow solution was diluted with ether, washed with 1 N NaOH, dried (MgSO$_4$), and concentrated in vacuo. The crude product was purified by flash column chromatography (hexane) to provide the product (5.2 g, 75%) as a colorless oil. $^1$H NMR (400 MHz, CDCl$_3$) δ 7.39-7.33 (m, 1H), 7.30 (dd, J=8.0, 3.0 Hz, 1H), 7.01-6.94 (m, 1H), 6.91-6.85 (m, 1H), 5.90 (ddt, J=17.2, 10.2, 7.0 Hz, 1H), 5.20-5.10 (m, 2H), 4.36 (sxt, J=6.1 Hz, 1H), 2.58-2.49 (m, 1H), 2.45-2.36 (m, 1H), 1.34 (d, J=6.0 Hz, 3H).

Intermediate 15

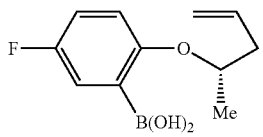 [SMILES: C=CC[C@H](C)Oc1ccc(F)cc1B(O)O]

(S)-(5-Fluoro-2-(pent-4-en-2-yloxy)phenyl)boronic Acid

A solution of (S)-2-bromo-4-fluoro-1-(pent-4-en-2-yloxy)benzene (4.5, 17.37 mmol) in THF (90 mL) was cooled to −78° C. (IPA/dry ice). nBuLi (13.03 mL of a 1.6 M solution in hexane, 20.84 mmol) was added slowly. After 30 min, triisopropyl borate (4.79 mL, 20.84 mmol) was added. The reaction was stirred 30 min and cold bath was removed. After 30 min at rt, 1 N HCl (25 mL) was added stirred for 10 min. Then, diluted with water (50 mL) and extracted with DCM (×3). The combined DCM extracts were dried (Na$_2$SO$_4$) and concentrated in vacuo to provide the crude boronic acid (3.89 g) which was used in the next step without purification.

Intermediate 16

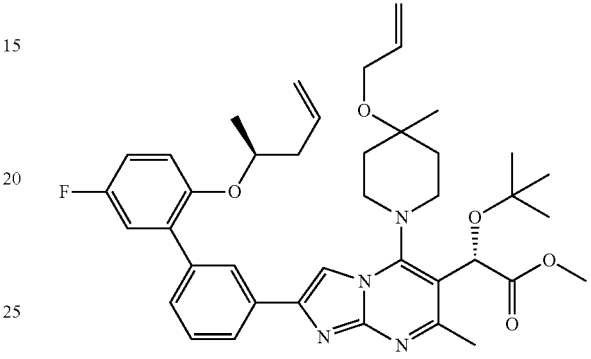

(S)-methyl 2-(5-(4-(allyloxy)-4-methylpiperidin-1-yl)-2-(5'-fluoro-2'-((S)-pent-4-en-2-yloxy)-[1,1'-biphenyl]-3-yl)-7-methylimidazo[1,2-a]pyrimidin-6-yl)-2-(tert-butoxy)acetate A solution of ((S)-methyl 2-(5-(4-(allyloxy)-4-methylpiperidin-1-yl)-2-(3-bromophenyl)-7-methylimidazo[1,2-a]pyrimidin-6-yl)-2-(tert-butoxy)acetate (100 mg, 0.171 mmol), (S)-(5-fluoro-2-(pent-4-en-2-yloxy)phenyl)boronic acid (77 mg, 0.342 mmol) and 2.0 M aq. Na2CO3 (0.213 mL, 0.427 mmol) in DMF (3 mL) was degassed for 10 min. Pd(Ph3P)4 (13.81 mg, 0.012 mmol), was added and the degassing was continued for another 5 min. The reaction was then heated at 90° C. for 3 hrs. At this point LCMS indicates completion of reaction. The mixture was then cooled to room temp and diluted with water (100 mL) and extracted with Et2O (2×250 mL). The combined extracts were dried (Na2SO4), filtered, and concentrated under reduced pressure, and the residue was purified by biotage (0-25% EtOAc/hexane) to afford (S)-methyl 2-(5-(4-(allyloxy)-4-methylpiperidin-1-yl)-2-(5'-fluoro-2'-((S)-pent-4-en-2-yloxy)-[1,1'-biphenyl]-3-yl)-7-methylimidazo[1,2-a]pyrimidin-6-yl)-2-(tert-butoxy)acetate (85 mg, 0.124 mmol, 72.7% yield) as white foam. Product seems to be the mixture of diastereomers. Major isomer transcribed. $^1$H NMR (500 MHz, CDCl$_3$) δ 8.12-8.03 (m, 2H), 7.94 (s, 1H), 7.58 (d, J=7.6 Hz, 1H), 7.49 (t, J=7.6 Hz, 1H), 7.18 (dd, J=9.1, 2.9 Hz, 1H), 7.04-6.92 (m, 2H), 6.13-5.98 (m, 1H), 5.94 (s, 1H), 5.74 (ddt, J=17.1, 10.2, 7.1 Hz, 1H), 5.43 (d, J=17.3 Hz, 1H), 5.12 (d, J=10.2 Hz, 1H), 5.04-4.97 (m, 2H), 4.27-4.17 (m, 1H), 4.01 (d, J=5.2 Hz, 2H), 3.97-3.89 (m, 1H), 3.73 (s, 3H), 3.10 (d, J=10.9 Hz, 1H), 2.79 (d, J=10.1 Hz, 1H), 2.71 (s, 3H), 2.42-2.34 (m, 1H), 2.30-2.21 (m, 1H), 2.01 (t, J=10.6 Hz, 2H), 1.84 (td, J=12.7, 4.7 Hz, 1H), 1.80-1.68 (m, 1H), 1.43-1.38 (m, 1H), 1.29 (s, 9H), 1.26 (s, 3H), 1.18 (d, J=6.0 Hz, 3H). LCMS (M+H)=685.4.

Example 2 and 3

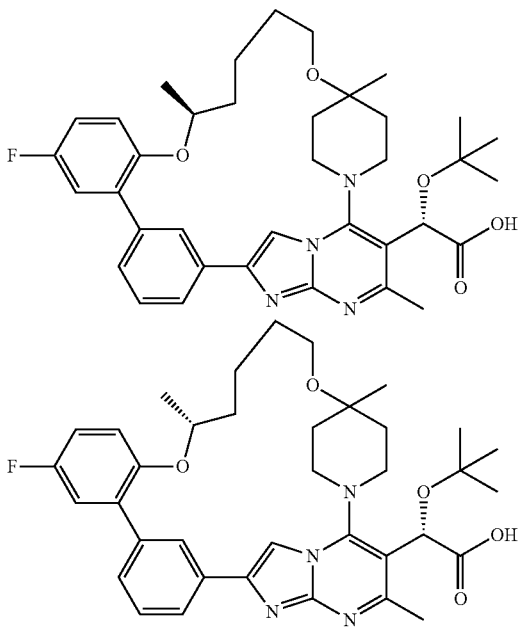

(2S)-2-(tert-butoxy)-2-[(22S/R)-17-fluoro-4,22,28-trimethyl-21,27-dioxa-1,5,7,34-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic Acid To a stirred solution of (S)-methyl 2-(5-(4-(allyloxy)-4-methylpiperidin-1-yl)-2-(5'-fluoro-2'-((S)-pent-4-en-2-yloxy)-[1,1'-biphenyl]-3-yl)-7-methylimidazo[1,2-a]pyrimidin-6-yl)-2-(tert-butoxy)acetate (80 mg, 0.117 mmol) and Ts-OH.H2O (22.22 mg, 0.117 mmol) in 1,2-Dichloroethane (80 mL) was added Hoveyda-Grubbs catalyst 2nd generation (7.32 mg, 0.012 mmol) and heated to 70° C. for 2 h. The reaction mixture was then cooled and concentrated to about 10 mL. To this solution was added EtOH (1 mL) and NaBH4 (22.10 mg, 0.584 mmol) at rt. Note: gas evoluved as soon as NaBH4 was added. After 30 min added additional NaBH4 (22.10 mg, 0.584 mmol) and the mixture was stirred for 16 h. LCMS at this point showed completion of reaction. The reaction mixture was diluted with EtOAc (50 mL), washed with water (3×10 mL), brine (5 mL), dried (Na2SO4), filtered and concentrated to give crude saturated ester as brown residue which was used in the next step without purification. LCMS (M+H)=659.4.

A mixture of above crude ester and 1N NaOH (0.584 mL, 0.584 mmol) in MeOH (2 mL) was refluxed for 4 h. Then, cooled and purified by prep-HPLC to afford two diastereomers.

Example 2

(2.7 mg, 4.19 μmol, 3.58% yield). $^1$H NMR (500 MHz, DMSO-d$_6$) δ 8.24 (s, 1H), 8.09 (d, J=7.7 Hz, 1H), 8.01-7.95 (m, 1H), 7.56 (t, J=7.7 Hz, 1H), 7.40 (d, J=7.7 Hz, 1H), 7.27-7.21 (m, 1H), 7.20-7.12 (m, 2H), 5.74 (s, 1H), 4.62 (br. s., 1H), 3.81 (t, J=11.0 Hz, 1H), 3.60 (t, J=11.0 Hz, 1H), 3.45-3.27 (m, 4H), 3.27 (d, J=7.7 Hz, 1H), 2.79-2.72 (m, 1H), 2.57 (s, 3H), 1.96 (d, J=13.2 Hz, 1H), 1.88-1.73 (m, 4H), 1.65-1.50 (m, 2H), 1.21 (s, 3H), 1.18 (s, 9H), 1.08 (d, J=6.2 Hz, 3H). LCMS (M+H)=645.5.

Example 3

(2.2 mg, 3.41 μmol, 2.92% yield). $^1$H NMR (500 MHz, DMSO-d$_6$) δ 8.14 (s, 1H), 8.07 (d, J=7.7 Hz, 1H), 7.89 (s, 1H), 7.57 (t, J=7.7 Hz, 1H), 7.41 (d, J=7.7 Hz, 1H), 7.24-7.13 (m, 3H), 5.86 (s, 1H), 4.57 (d, J=4.8 Hz, 1H), 3.78 (t, J=11.2 Hz, 1H), 3.66-3.58 (m, 1H), 3.52-3.40 (m, 2H), 3.36 (br. s., 1H), 2.97 (d, J=9.2 Hz, 1H), 2.81 (d, J=10.6 Hz, 1H), 2.61 (s, 3H), 1.96-1.72 (m, 5H), 1.72-1.62 (m, 3H), 1.53 (br. s., 1H), 1.22 (br. s., 3H), 1.21 (s, 9H), 1.10 (d, J=5.9 Hz, 3H). LCMS (M+H)=659.4.

The following examples could be prepared by person skilled in the art by following the procedures known in the art or as set forth in the examples 1-3.

Example 4

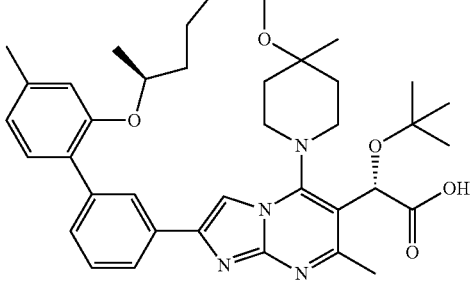

(2S)-2-(tert-Butoxy)-2-[(22S)-4,18,22,28-tetramethyl-21,27-dioxa-1,5,7,34-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic Acid

Example 5

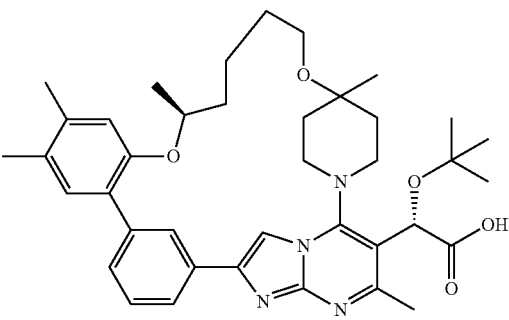

31

(2S)-2-(tert-Butoxy)-2-[(22S)-4,17,18,22,28-pentamethyl-21,27-dioxa-1,5,7,34-tetraazahexacyclo [26.2.2.1$^{6,9}$.1$^{10,14}$.0$^{2,7}$.0$^{15,20}$]tetratriaconta-2,4,6 (34),8,10(33),11,13,15(20),16,18-decaen-3-yl]acetic acid Example 6

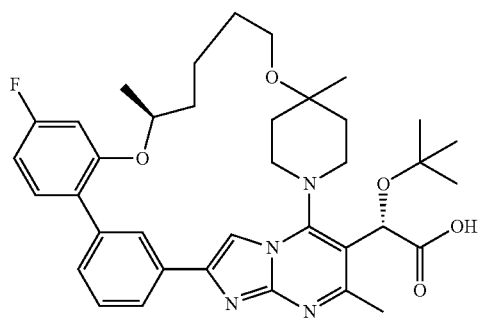 [SMILES: Cc1ccc2c(c1)O[C@@H](C)CCCCOC1(C)CCN(CC1)c1c([C@H](OC(C)(C)C)C(=O)O)c(C)nc3nc(cn13)-c1cccc-2c1]

(2S)-2-(tert-Butoxy)-2-[(22S)-18-fluoro-4,22,28-trimethyl-21,27-dioxa-1,5,7,34-tetraazahexacyclo [26.2.2.1$^{6,9}$.1$^{10,14}$.0$^{2,7}$.0$^{15,20}$]tetratriaconta-2,4,6 (34),8,10(33),11,13,15(20),16,18-decaen-3-yl]acetic Acid Example 7

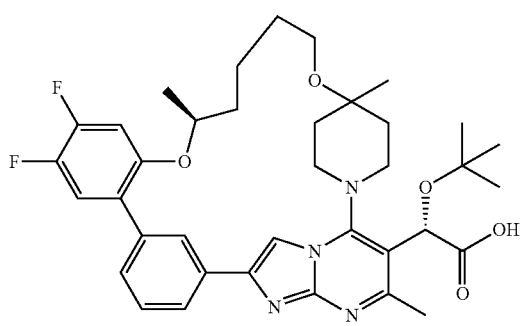 [SMILES: Cc1nc2nc3cn2c(c1[C@H](OC(C)(C)C)C(=O)O)N1CCC(C)(CC1)OCCCC[C@H](C)Oc1cc(F)c(F)cc1-c1cccc-3c1]

32

(2S)-2-(tert-Butoxy)-2-[(22S)-17,18-difluoro-4,22, 28-trimethyl-21,27-dioxa-1,5,7,34-tetraazahexacyclo [26.2.2.1$^{6,9}$.1$^{10,14}$.0$^{2,7}$.0$^{15,20}$]tetratriaconta-2,4,6 (34),8,10(33),11,13,15(20),16,18-decaen-3-yl]acetic Acid Example 8

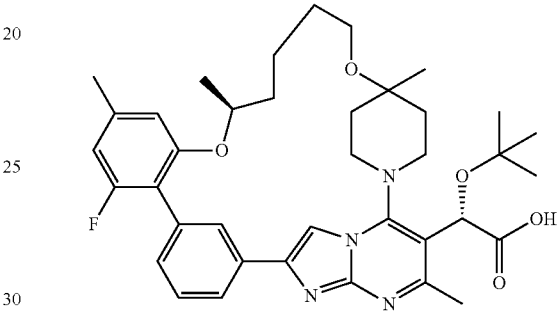

(2S)-2-(tert-Butoxy)-2-[(22S)-16-fluoro-4,18,22,28-tetramethyl-21,27-dioxa-1,5,7,34-tetraazahexacyclo [26.2.2.1$^{6,9}$.1$^{10,14}$.0$^{2,7}$.0$^{15,20}$]tetratriaconta-2,4,6 (34),8,10(33),11,13,15(20),16,18-decaen-3-yl]acetic Acid Example 9

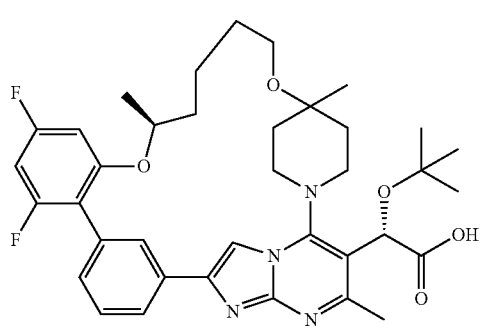 [SMILES: Cc1nc2nc3cn2c(c1[C@H](OC(C)(C)C)C(=O)O)N1CCC(C)(CC1)OCCCC[C@H](C)Oc1cc(F)cc(F)c1-c1cccc-3c1]

33

(2S)-2-(tert-Butoxy)-2-[(22S)-16,18-difluoro-4,22,28-trimethyl-21,27-dioxa-1,5,7,34-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic Acid Example 10

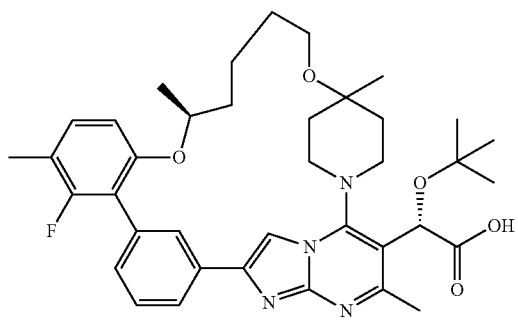 [SMILES: Cc1ccc2c(c1F)-c1cccc(c1)-c1cn3c(c([C@H](OC(C)(C)C)C(=O)O)c(C)nc3n1)N1CCC(C)(CC1)OCCCC[C@H](C)O2]

(2S)-2-(tert-Butoxy)-2-[(22S)-16-fluoro-4,17,22,28-tetramethyl-21,27-dioxa-1,5,7,34-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic Acid Example 11

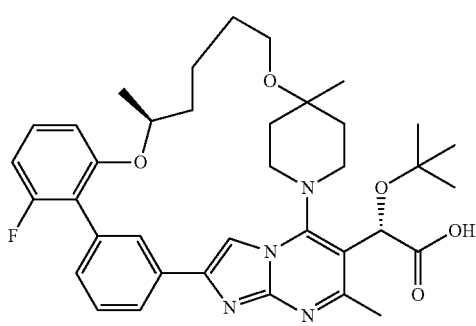 [SMILES: Cc1nc2nc3cn2c(c1[C@H](OC(C)(C)C)C(=O)O)N1CCC(C)(CC1)OCCCC[C@H](C)Oc1cccc(F)c1-c1cccc-3c1]

34

(2S)-2-(tert-Butoxy)-2-[(22S)-16-fluoro-4,22,28-trimethyl-21,27-dioxa-1,5,7,34-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic Acid Example 12

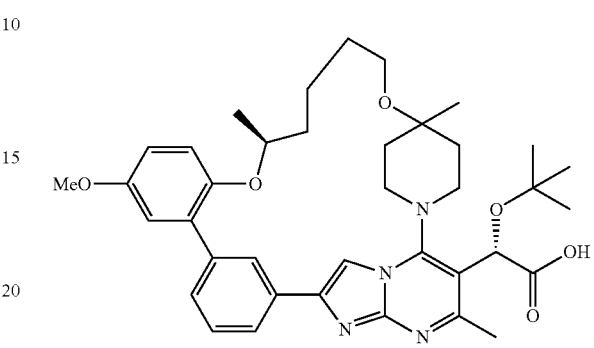

(2S)-2-(tert-Butoxy)-2-[(22S)-17-methoxy-4,22,28-trimethyl-21,27-dioxa-1,5,7,34-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic Acid It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

We claim:
1. A compound of Formula I

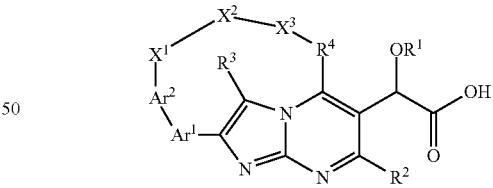

where:
$R^1$ is hydrogen, alkyl, or cycloalkyl;
$R^2$ is hydrogen or alkyl;
$R^3$ is hydrogen, alkyl or halo;
$R^4$ is cycloalkyl or $Ar^3$;
or $R^4$ is azetidinyl, pyrrolidinyl, piperidinyl, piperazinyl, morpholinyl, homopiperidinyl, homopiperazinyl, or homomorpholinyl, and is substituted with 0-3 alkyl substituents;
$R^5$ is hydrogen or alkyl;
$Ar^1$ is phenyl substituted with 0-3 substituents selected from cyano, halo, alkyl, haloalkyl, alkoxy, and haloalkoxy;

Ar² is phenyl, pyridinyl, pyridazinyl, pyrimidinyl, pyrazinyl, or triazinyl, and is substituted with 0-3 substituents selected from cyano, halo, alkyl, haloalkyl, alkoxy, haloalkoxy, and CON(R⁵)₂;

Ar³ is phenyl, chromanyl, or dihydrobenzoxazinyl, and is substituted with 0-3 substituents selected from cyano, halo, alkyl, haloalkyl, alkoxy, and haloalkoxy;

$X^1$ is CH, $CH_2$, O, S, or $NR^5$;

$X^2$ is alkylene or alkenylene; and $X^3$ is CH, $CH_2$, $CH_2O$, O, S, or $NR^5$;

or a pharmaceutically acceptable salt thereof.

2. A compound of claim 1 where $R^1$ is alkyl; $R^2$ is alkyl; $R^3$ is hydrogen; $R^4$ is $Ar^3$ or is azetidinyl, pyrrolidinyl, piperidinyl, piperazinyl, morpholinyl, homopiperidinyl, homopiperazinyl, or homomorpholinyl substituted with 0-3 alkyl substituents; $Ar^1$ is phenyl substituted with 0-3 substituents selected from cyano, halo, alkyl, haloalkyl, alkoxy, and haloalkoxy; $Ar^2$ is phenyl substituted with 0-3 substituents selected from selected from cyano, halo, alkyl, haloalkyl, alkoxy, haloalkoxy, and CON(R⁵)₂; $Ar^3$ is dihydrobenzoxazinyl substituted with 0-3 substituents selected from cyano, halo, alkyl, haloalkyl, alkoxy, and haloalkoxy; $X^1$ is $CH_2$ or O; $X^2$ is alkylene or alkenylene; and $X^3$ is CH, $CH_2$ or O; or a pharmaceutically acceptable salt thereof.

3. A compound of claim 2 where $R^1$ is alkyl; $R^2$ is alkyl; $R^3$ is hydrogen; $R^4$ is piperidinyl substituted with 0-1 alkyl substituents; $Ar^1$ is phenyl; $Ar^2$ is phenyl substituted with 0-3 substituents selected from cyano, halo, alkyl, haloalkyl, alkoxy, haloalkoxy, and CON(R⁵)₂; $X^1$ is $CH_2$ or O; $X^2$ is alkylene or alkenylene; and $X^3$ is CH, $CH_2$ or O; or a pharmaceutically acceptable salt thereof.

4. A compound of claim 1 where $R^1$ is alkyl, $R^2$ is alkyl and $R^3$ is hydrogen.

5. A compound of claim 1 where $R^4$ is piperidinyl substituted with 0-3 alkyl substituents.

6. A compound of claim 1 where $Ar^1$ is phenyl.

7. A compound of claim 1 where $Ar^2$ is phenyl substituted with 0-3 substituents selected from cyano, halo, alkyl, haloalkyl, alkoxy, haloalkoxy, and CON(R⁵)₂.

8. A compound of claim 1 where $Ar^3$ is chromanyl or dihydrobenzoxazinyl, and is substituted with 0-3 substituents selected from cyano, halo, alkyl, haloalkyl, alkoxy, and haloalkoxy.

9. A compound of claim 1 where $X^1$ is $CH_2$ or O; $X^2$ is alkylene or alkenylene; and $X^3$ is CH, $CH_2$ or O.

10. A compound of claim 1 selected from the group consisting of (2S)-2-(tert-Butoxy)-2-[(22S)-4,17,22,28-tetramethyl-21,27-dioxa-1,5,7,34-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid;

(2S)-2-(tert-Butoxy)-2-[(22S)-4,18,22,28-tetramethyl-21,27-dioxa-1,5,7,34-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid;

(2S)-2-(tert-Butoxy)-2-[(22S)-4,17,18,22,28-pentamethyl-21,27-dioxa-1,5,7,34-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid;

(2S)-2-(tert-Butoxy)-2-[(22S)-17-fluoro-4,22,28-trimethyl-21,27-dioxa-1,5,7,34-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid;

(2S)-2-(tert-Butoxy)-2-[(22S)-18-fluoro-4,22,28-trimethyl-21,27-dioxa-1,5,7,34-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid;

(2S)-2-(tert-Butoxy)-2-[(22S)-17,18-difluoro-4,22,28-trimethyl-21,27-dioxa-1,5,7,34-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid;

(2S)-2-(tert-Butoxy)-2-[(22S)-16-fluoro-4,18,22,28-tetramethyl-21,27-dioxa-1,5,7,34-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid;

(2S)-2-(tert-Butoxy)-2-[(22S)-16,18-difluoro-4,22,28-trimethyl-21,27-dioxa-1,5,7,34-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid;

(2S)-2-(tert-Butoxy)-2-[(22S)-16-fluoro-4,17,22,28-tetramethyl-21,27-dioxa-1,5,7,34-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid;

(2S)-2-(tert-Butoxy)-2-[(22S)-16-fluoro-4,22,28-trimethyl-21,27-dioxa-1,5,7,34-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid; and (2S)-2-(tert-Butoxy)-2-[(22S)-17-methoxy-4,22,28-trimethyl-21,27-dioxa-1,5,7,34-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid;

or a pharmaceutically acceptable salt thereof.

11. A composition useful for treating HIV infection comprising a therapeutic amount of a compound of claim 1 and a pharmaceutically acceptable carrier.

12. A method for treating HIV infection comprising administering a therapeutically effective amount of a compound of claim 1, or a pharmaceutically acceptable salt thereof, to a patient in need thereof.

13. The method of claim 12 further comprising administering a therapeutically effective amount of at least one other agent used for treatment of AIDS or HIV infection selected from the group consisting of nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors.

* * * * *